US009693864B1

United States Patent
Naficy

(10) Patent No.: US 9,693,864 B1
(45) Date of Patent: Jul. 4, 2017

(54) HEART SURGERY APPARATUS

(71) Applicant: Mohammad A. Naficy, Potomac, MD (US)

(72) Inventor: Mohammad A. Naficy, Potomac, MD (US)

(73) Assignee: Mohammad Naficy, Potomac, MD (US)

( * ) Notice: Subject to any disclaimer, the term of this patent is extended or adjusted under 35 U.S.C. 154(b) by 0 days.

(21) Appl. No.: 15/084,540

(22) Filed: Mar. 30, 2016

(51) Int. Cl.
*A61F 2/24* (2006.01)
*A61B 1/04* (2006.01)
*A61B 1/06* (2006.01)

(52) U.S. Cl.
CPC .............. *A61F 2/2466* (2013.01); *A61B 1/04* (2013.01); *A61B 1/06* (2013.01); *A61F 2/2445* (2013.01); *A61F 2220/0075* (2013.01); *A61F 2310/00023* (2013.01)

(58) Field of Classification Search
CPC ... A61F 2/2457; A61F 2017/2808–2017/2948; A61B 17/28–17/295; A61B 17/128–17/1285; A61B 17/1227
See application file for complete search history.

(56) References Cited

U.S. PATENT DOCUMENTS

| | | | | |
|---|---|---|---|---|
| 4,919,152 A | * | 4/1990 | Ger | A61B 17/29 128/898 |
| 6,322,578 B1 | * | 11/2001 | Houle | A61B 17/2909 600/564 |
| 2006/0167474 A1 | * | 7/2006 | Bloom | A61F 2/2466 606/142 |
| 2009/0177274 A1 | * | 7/2009 | Scorsin | A61F 2/2457 623/2.1 |
| 2013/0197630 A1 | * | 8/2013 | Azarnoush | A61F 2/2457 623/2.17 |
| 2015/0094800 A1 | * | 4/2015 | Chawla | A61F 2/2457 623/2.1 |

* cited by examiner

*Primary Examiner* — Victor Nguyen
*Assistant Examiner* — Jonathan Hollm
(74) *Attorney, Agent, or Firm* — Maxvalueip LLC

(57) ABSTRACT

In one example, we describe an apparatus for heart surgery that enables the surgeon do the attachment for torn tissue or connector for the bottom end, located inside the heart, from left atrium, with ease. Thus, it reduces the problem drastically, with lower risk and lower failure rate. Different variations are shown here, with various examples. This is a very valuable tool for the heart surgeons. The light and camera are optional features for the surgeon's installer tool.

19 Claims, 46 Drawing Sheets

Sewed & bring it down & repair valve (for competence valve)

Plug in

HEART SURGERY APPARATUS

BACKGROUND OF THE INVENTION

In a normal heart, we have mitral valve that consists of leaflet and papillary muscle, as well as chords, which control the closing of the one-way valves, as shown in FIG. 36. However, when there is a heart attack, and the chord and muscles are damaged, then the mechanism to close the valve is not working anymore. Thus, one has to reconnect and repair that. Traditionally, the surgeon goes inside the heart and does the attachment on both sides of the torn or ruptured corde (connection), by stitching or sewing the "connector" from both ends, to resume the connectivity and functionality of the valve. This is hard to do, as the bottom part of the connector is inside the heart, and it is, therefore, hard to see and access. The valves may get damaged, as well, which then, have to be replaced altogether, which is bad for the patient.

Thus, it is desirable to find an apparatus that facilitates the connection for the bottom part of the corde (connector) inside the heart, to reduce the risk and failure rate. This is the subject of this invention. However, the invention and embodiments described here, below, have not been addressed or presented, in any prior art.

SUMMARY OF THE INVENTION

In one embodiment, we describe an apparatus for heart surgery that enables the surgeon do the attachment for torn tissue or connector for the bottom end, located inside the heart, from left atrium, with ease. Thus, it reduces the problem drastically, with lower risk and lower failure rate. Different variations are shown here, with various examples. This is a very valuable tool for the heart surgeons, as the inventor himself is a heart surgeon, with lots of experience. The light and camera are optional features for the surgeon's installer tool.

DETAILED DESCRIPTION OF THE PREFERRED EMBODIMENTS

Figure 36:
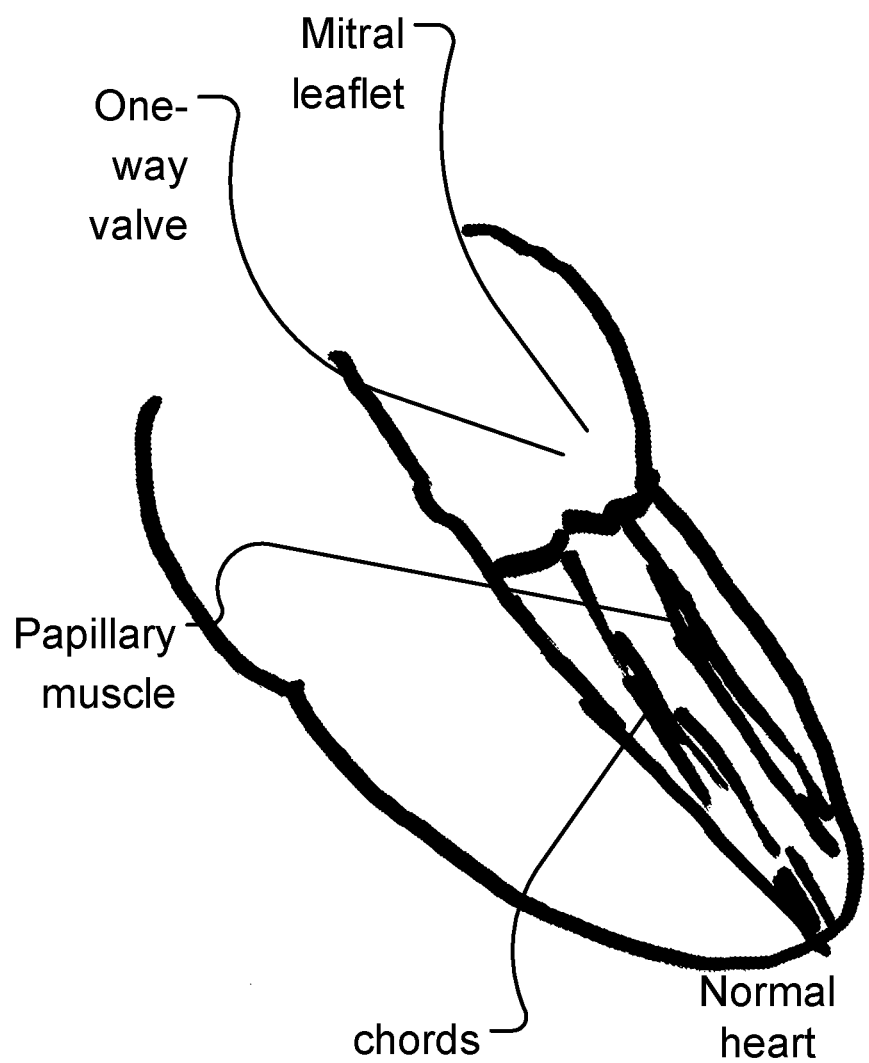
FIG. 36 is as an example for normal heart components.
Figure 37:
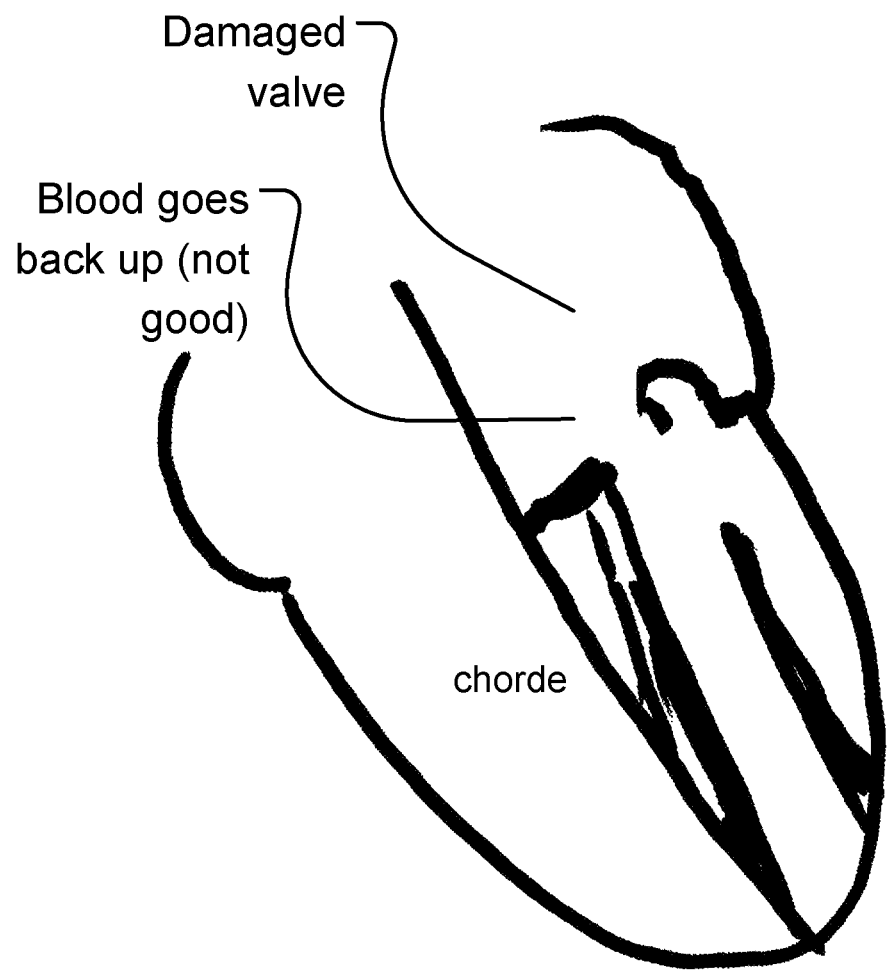
FIG. 37 is as an example for damaged heart components.

FIG. 36 is as an example for normal heart components, with mitral leaflet, one-way valves, papillary muscle, chords, and different chambers or sections of the heart. FIG. 37 is as an example for damaged heart components, with torn connectors for valves, due to, e.g., heart attack, causing a loose valve and blood backing/going up through the loose valve that cannot stop the backflow, which is a very bad situation for the patient.

Figure 3:
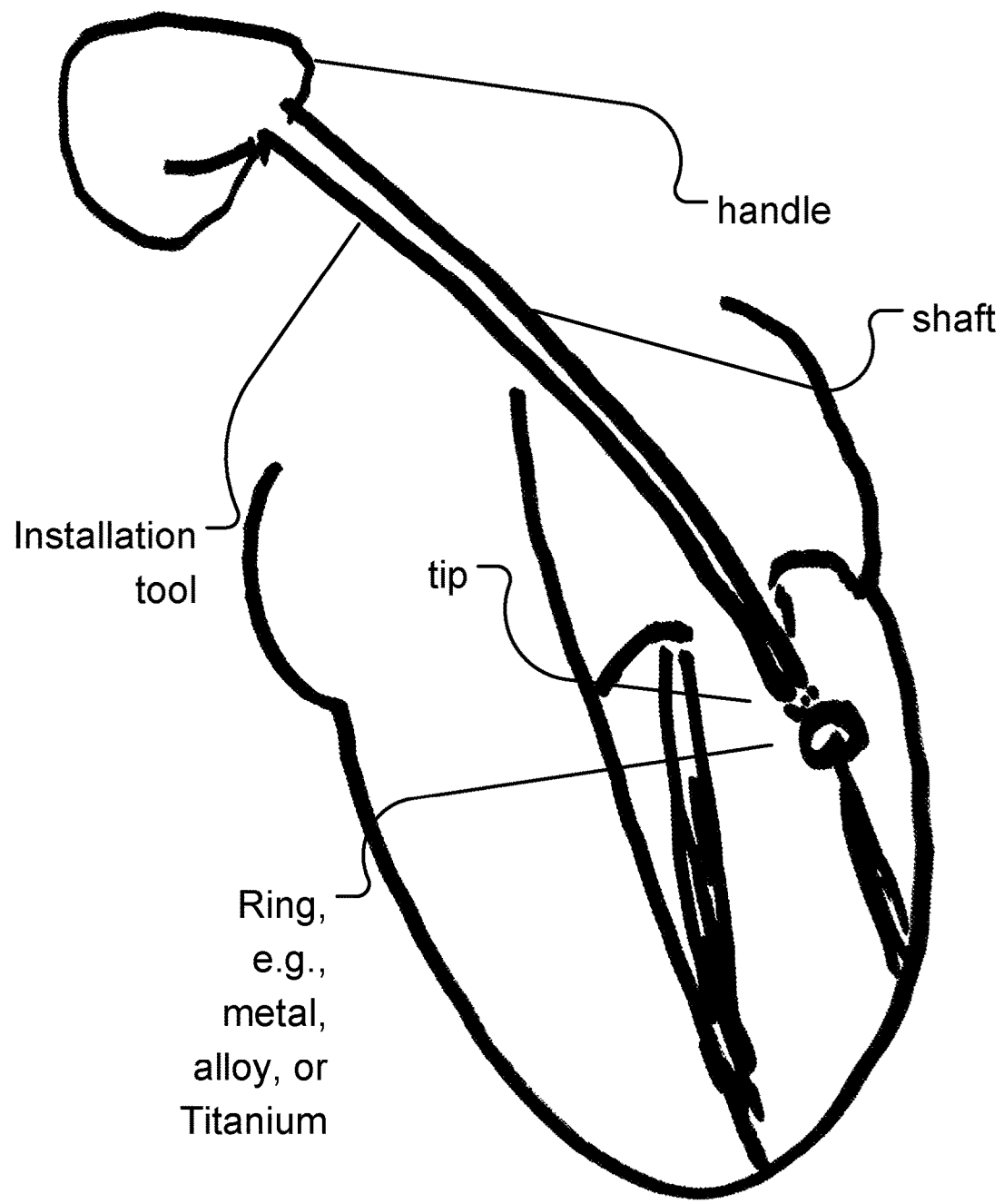
FIG. 3 is for one embodiment, as an example, for repairing heart components, using our apparatus, the installation tool.

FIG. 3 is for one embodiment, as an example, for repairing heart components or connection, using our apparatus, the installation tool, with handle and shaft, with tip hooking or connecting to or carrying a ring or equivalent, to connect/ attach to the lower portion, by any of the methods shown here or well-known or their equivalents or obvious variations, within the heart, which is otherwise very difficult to do, by surgeon, due to low visibility and access inside the heart.

The ring can be Titanium, other metals, alloys, plastic, natural or man-made materials, or any other known material currently in use for surgery or implantation for humans or animals, which is not toxic or have a bad reaction from the patient body or have allergy to it.

Figure 4:
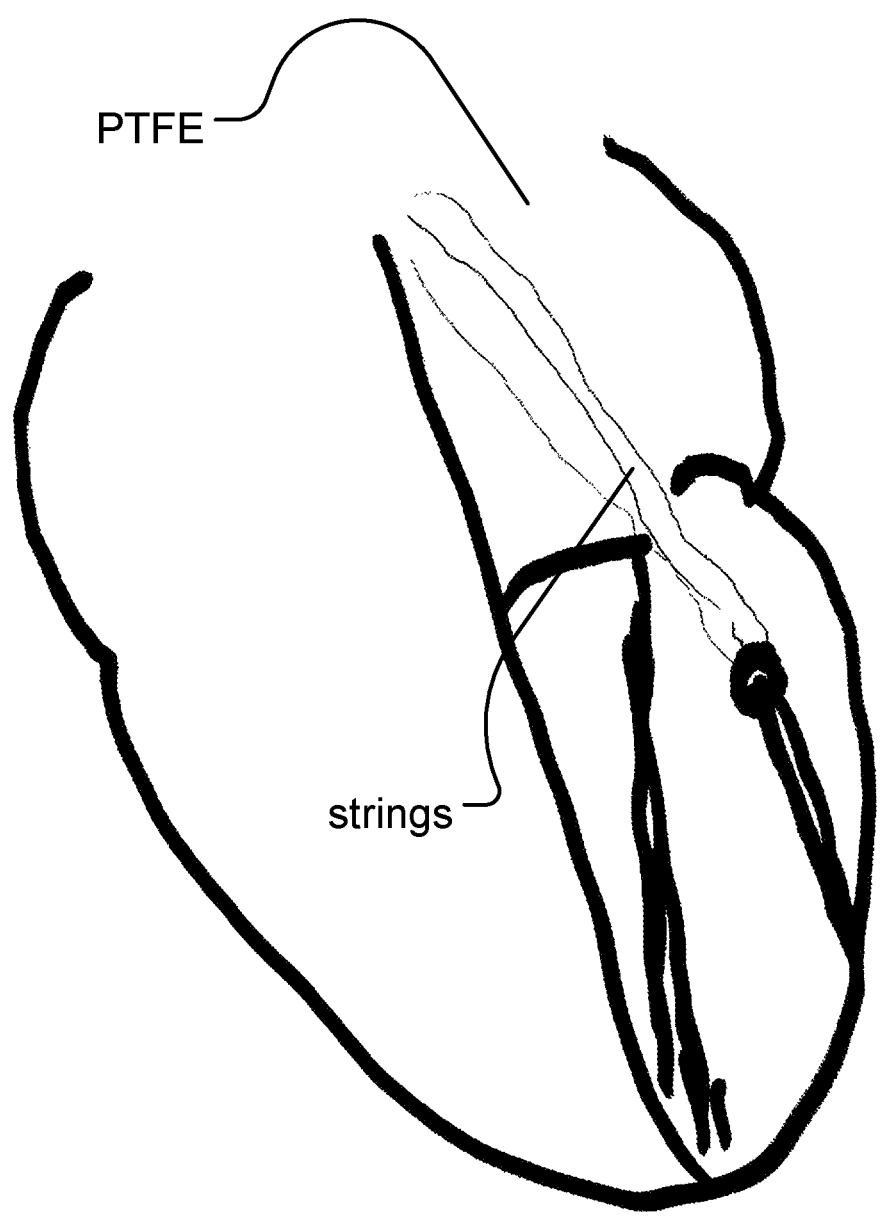
FIG. 4 is for one embodiment, as an example, for repairing heart components, using a ring attached to one or more strings, with ring attached or affixed to the bottom portion, inside the heart.
Figure 5:
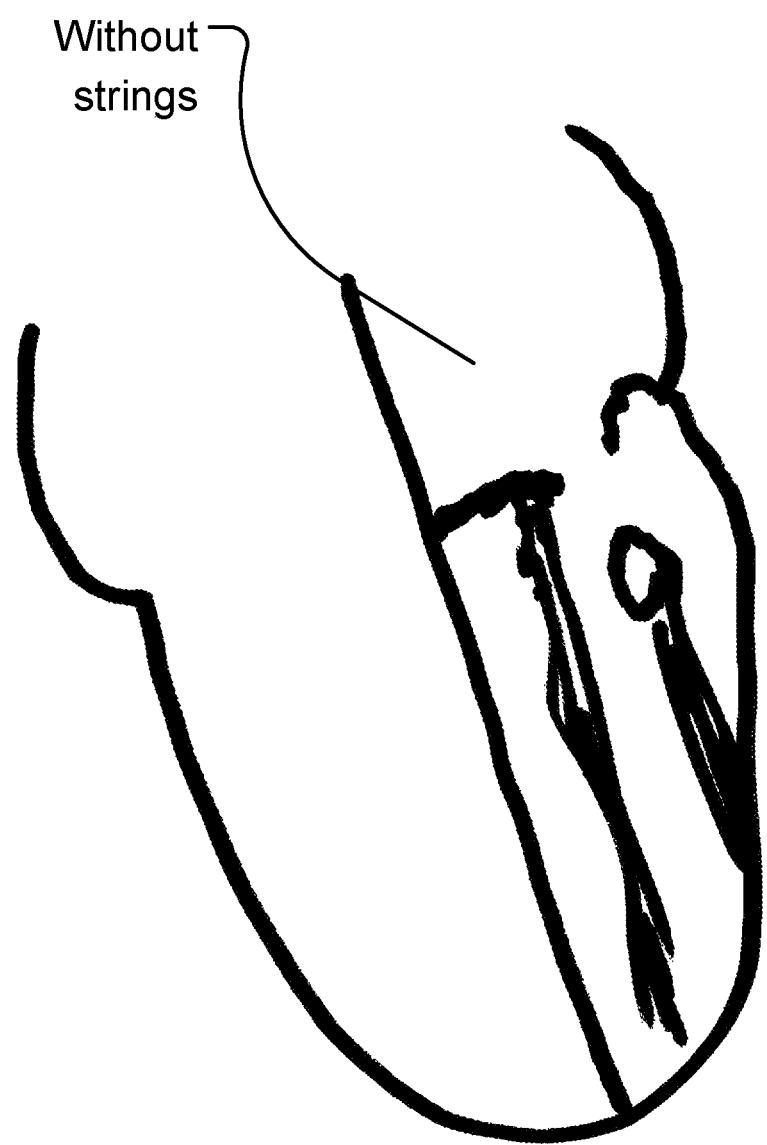
FIG. 5 is for one embodiment, as an example, for repairing heart components, using the ring, without showing the strings for this figure.

FIG. 4 is for one embodiment, as an example, for repairing heart components, using a ring or equivalent attached to one or more strings (or bands, strips, hooks, connectors, belts, buckle-type, zipper-type, stitches-type, or knot-type/form), with ring attached or affixed to the bottom portion, inside the heart. The string material is PTFE, polytetrafluoroethylene, prolene, plastic type, artificial materials, Gore-Tex, or any durable known material currently in use for surgery or implantation or stitches for humans or animals, which is not toxic or have a bad reaction from the patient body or have allergy to it. FIG. 5 is for one embodiment, as an example, for repairing heart components, using the ring, without showing the strings for this figure for clarity.

Figure 6:
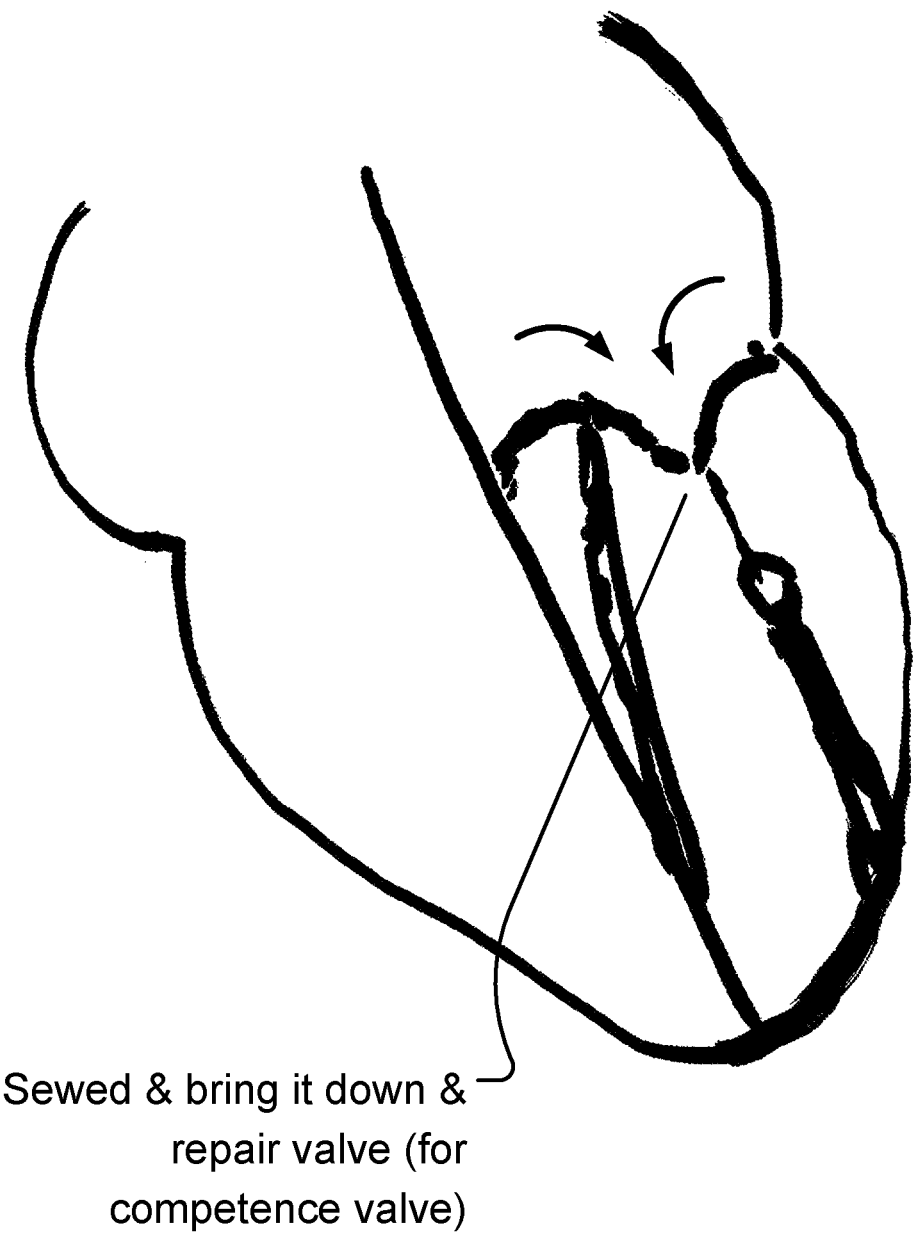
FIG. 6 is for one embodiment, as an example, for repairing heart components, using the ring and stitches on the top section/end, after the ring was attached to the bottom section, using staple-form or stitches or clamp or pressure-based half-rings or clamped ring or clamped 2-half-pieces or other methods shown in this disclosure or the obvious variations of those.

FIG. 6 is for one embodiment, as an example, for repairing heart components, using the ring and stitches, or their equivalents, on the top section/end, after the ring was attached to the bottom section, using staple-form or stitches or sutures or clamp or pressure-based half-rings or clamped ring or clamped 2-half-pieces or other methods shown in this disclosure or the obvious variations of those or the well-known methods in the industry for surgery or connectivity, or their equivalents. So, the loose valve is now sewed or stitched or attached or connected, to pull down the valve to the right place, for proper functionality.

Figure 7:
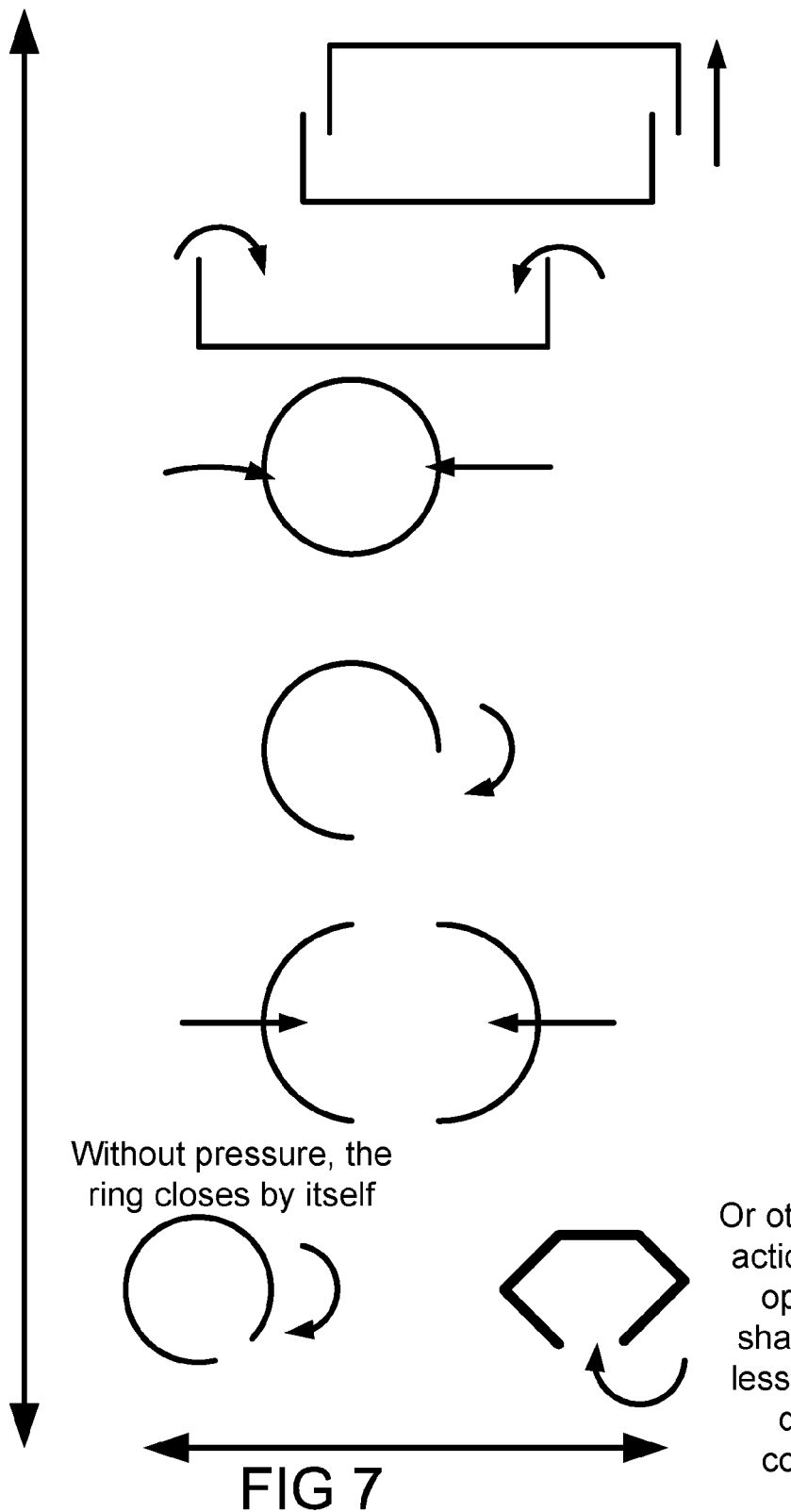
FIG. 7 is for one embodiment, as an example, for rings, staples, half-rings, and their multiple variations.
Figure 8:
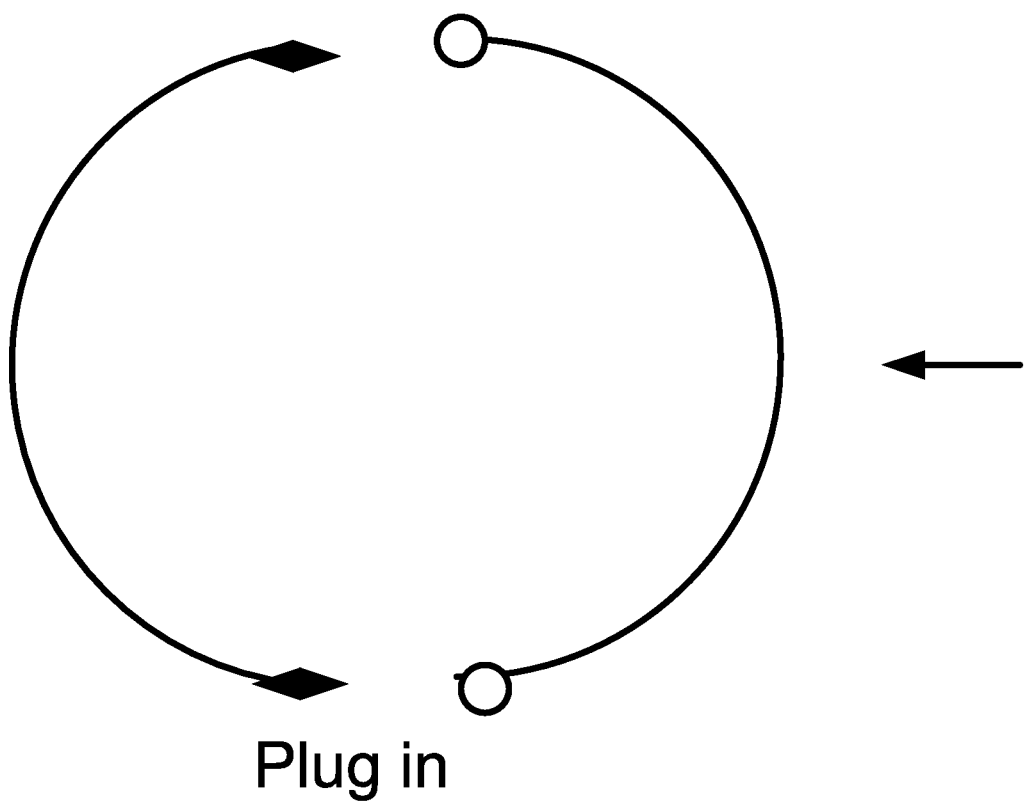
FIG. 8 is for one embodiment, as an example, for 2-half-rings, and how they attach to each other, with arrow heads or diamond extensions.

FIG. 7 is for one embodiment, as an example, for rings, staples, half-rings, open-rings, complementary-rectangles or boxes, to join or lock in or snap together, and their multiple variations. FIG. 8 is for one embodiment, as an example, for 2-half-rings, and how they attach to each other, with arrow heads or diamond extensions, through the holes, to grab and fit in, for enough friction to hold, as a circle or ring, attached to tissues, in the heart, as shown in the other figures here.

Figure 9:
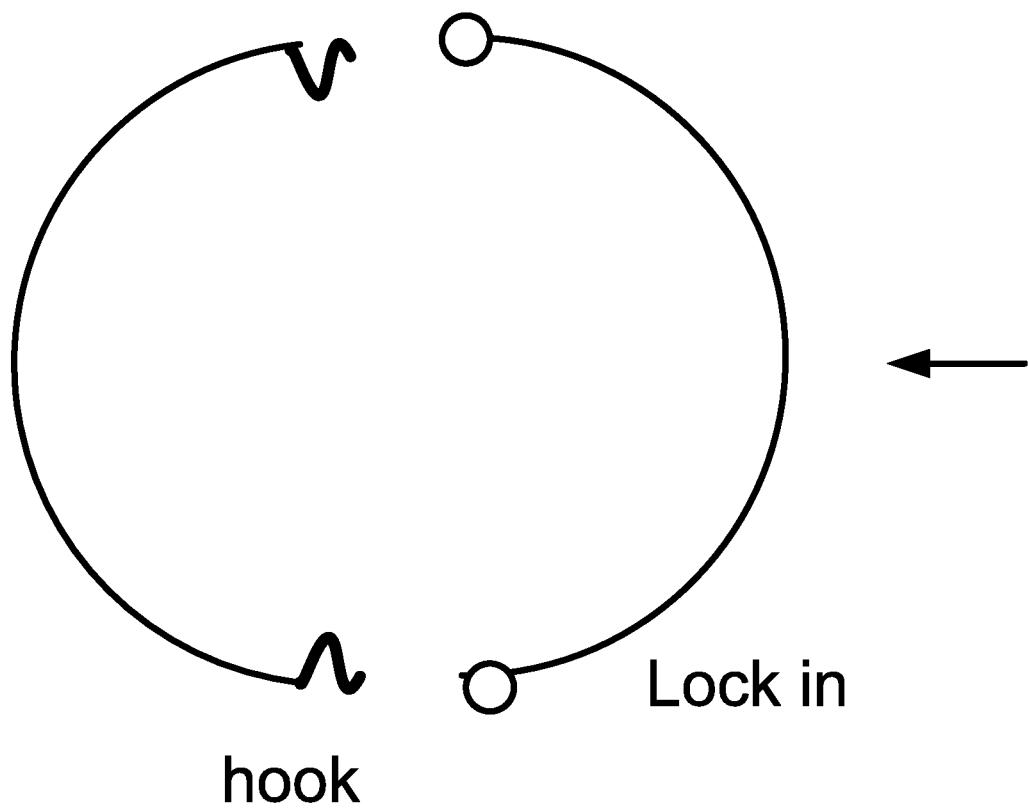
FIG. 9 is for one embodiment, as an example, for 2-half-rings, and how they attach to each other, with hooks or wiggly connections.
Figure 10:
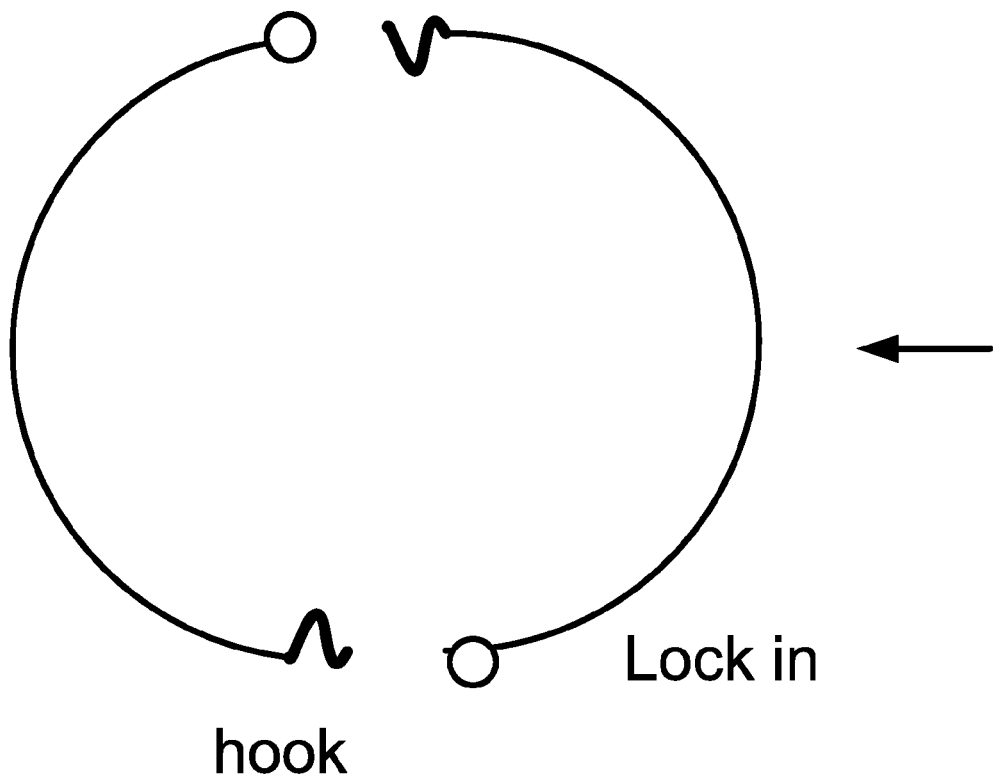
FIG. 10 is for one embodiment, as an example, for 2-half-rings, and how they attach to each other, with hooks or wiggly connections, as alternative to FIG. 9 and FIG. 8.

FIG. 9 is for one embodiment, as an example, for 2-half-rings, and how they attach to each other, with hooks or wiggly connections, to lock in. FIG. 10 is for one embodiment, as an example, for 2-half-rings, and how they attach to each other, with hooks or wiggly connections, as alternative to FIG. 9 and FIG. 8.

Figure 11:
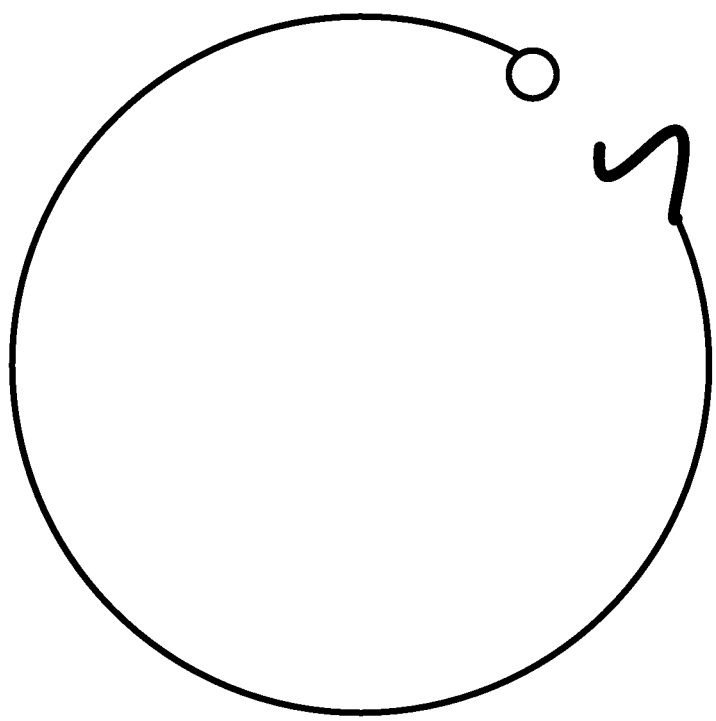
FIG. 11 is for one embodiment, as an example, for full-ring, and how it closes, with hooks or wiggly connections.
Figure 12:
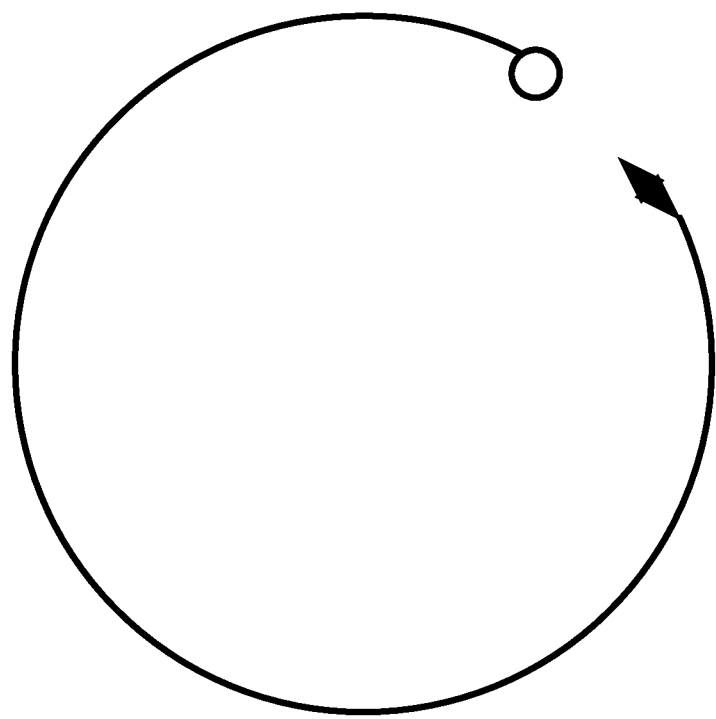
FIG. 12 is for one embodiment, as an example, for full-ring, and how it closes, with arrow heads or diamond extensions, for tips, for locking system.

FIG. 11 is for one embodiment, as an example, for full-ring, and how it closes, with hooks or wiggly connections, or equivalents, to grab and stay in, with pressure or friction, with tissue, after surgery. FIG. 12 is for one embodiment, as an example, for full-ring, and how it closes, with arrow heads or diamond extensions, for tips, for locking system.

Figure 13:
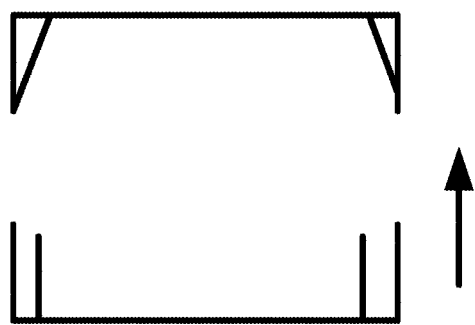
FIG. 13 is for one embodiment, as an example, for rectangular forms or pieces, and how it closes, with inclined surface or wedges, for locking system, inside each other, with male-female pieces, under pressure and friction, for stability and locking purpose.

FIG. 13 is for one embodiment, as an example, for rectangular forms or pieces, and how it closes, with inclined surface or wedges, for locking system, inside each other, with male-female pieces, under pressure and friction, for stability and locking purpose, within heart, on tissue.

Figure 14:
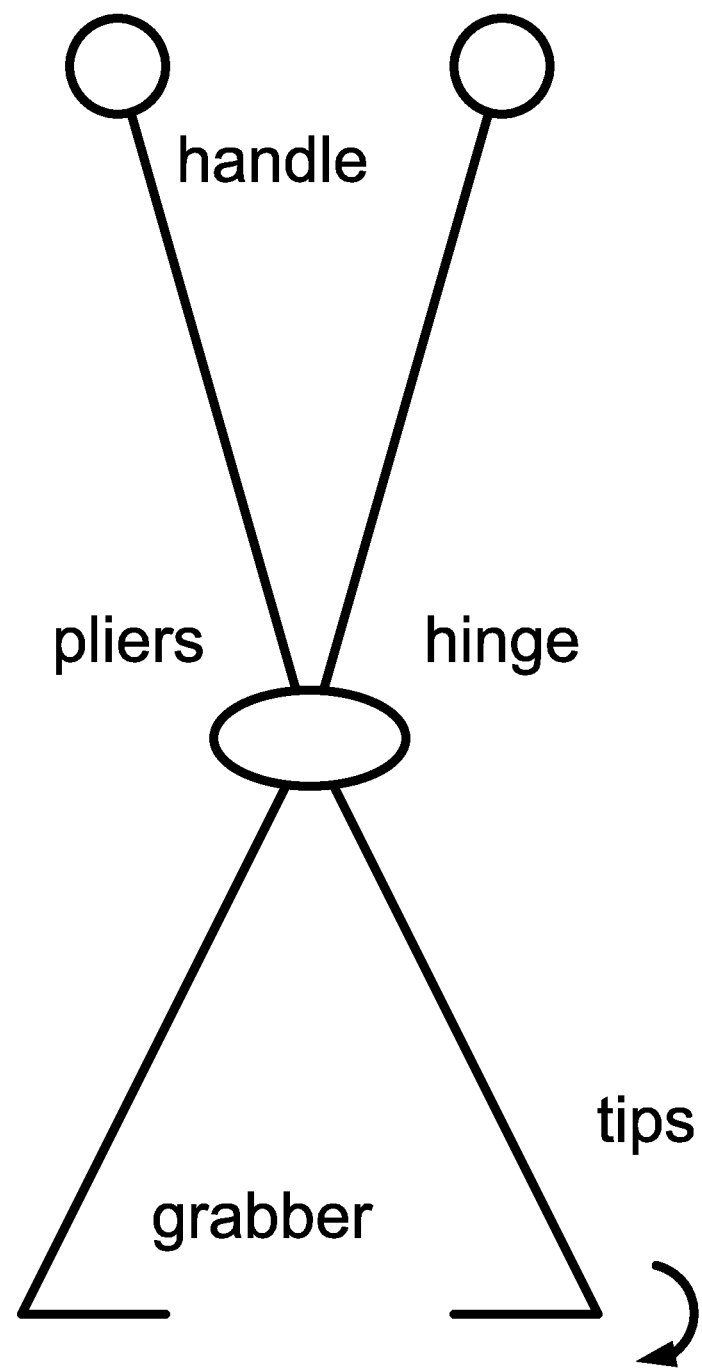
FIG. 14 is for one embodiment, as an example, for installation tool, e.g., to install or attach the ring or half-rings.
Figure 15:
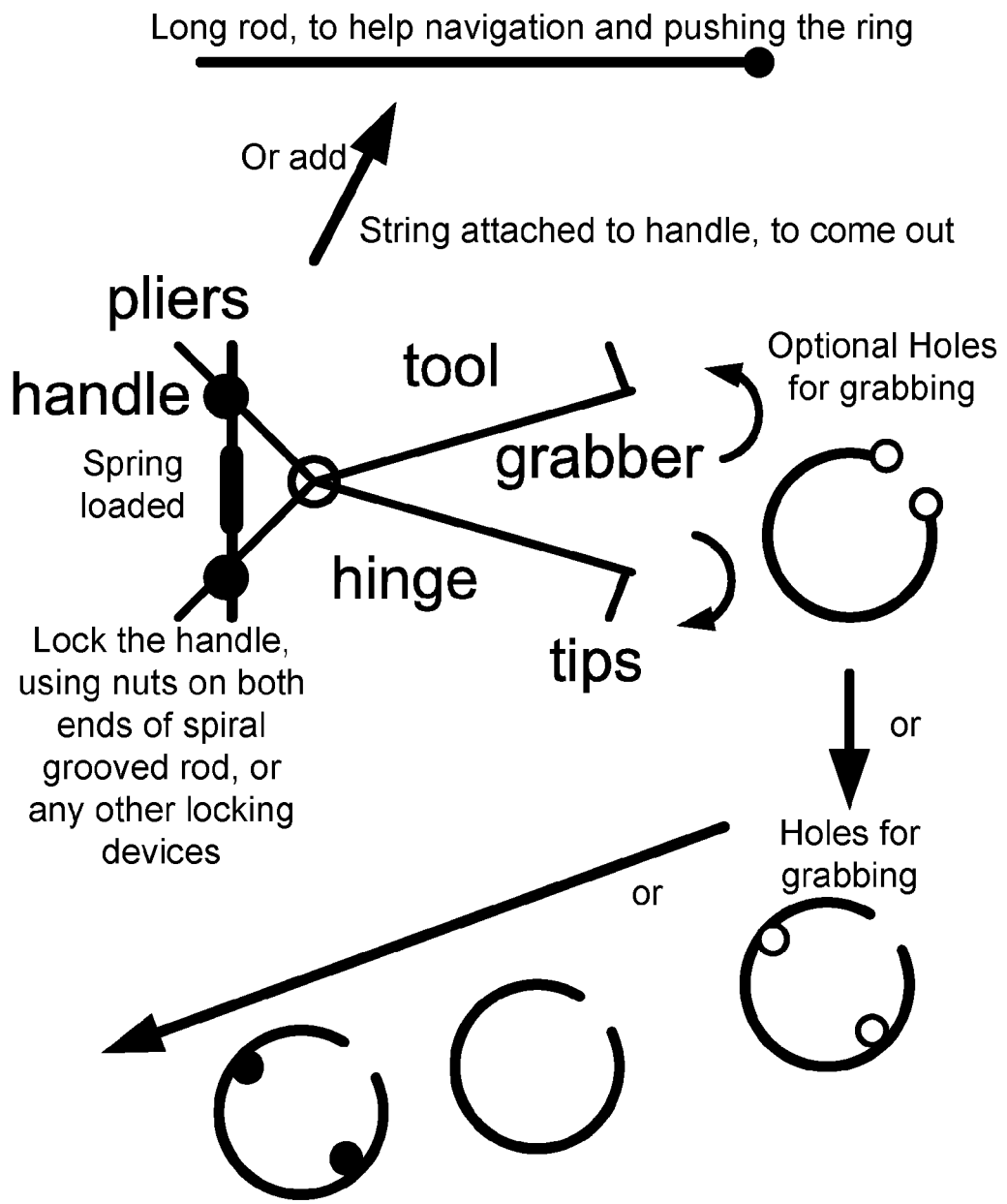
FIG. 15 is for one embodiment, as an example, for installer device, using locking device, for better control by surgeon.

FIG. 14 is for one embodiment, as an example, for installation tool, e.g., to install or attach the ring or half-rings or equivalents, with pliers-like structure with hinge, tips, grabber, and handle. FIG. 15 is for one embodiment, as an example, for installer device, using locking device, for better control by surgeon. The material for this is explained above.

Figure 16:
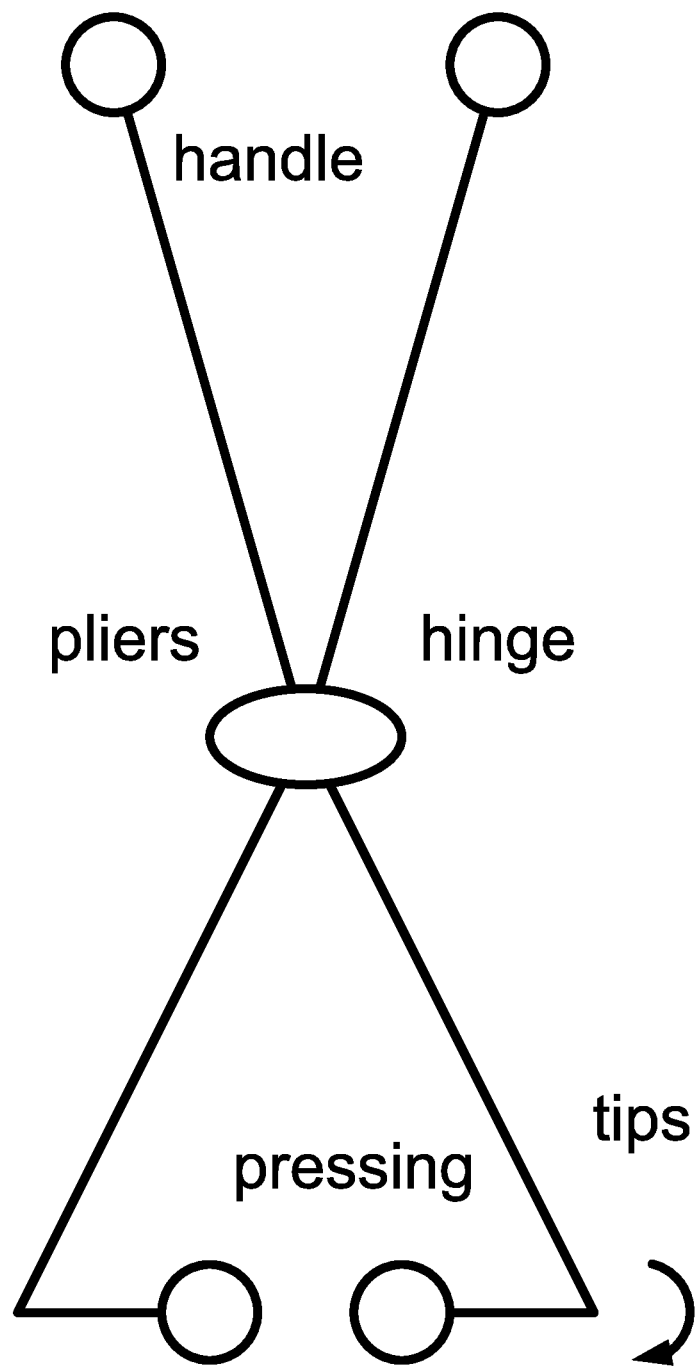
FIG. 16 is for one embodiment, as an example, for installation tool, e.g., to install or attach the ring or half-rings.

FIG. 16 is for one embodiment, as an example, for installation tool, e.g., to install or attach the ring or half-rings, similar to FIG. 14, but with a different tip ending, for flattening and pressuring on ring or equivalents, to close, secure, lock, attach, or install the ring or equivalents.

Figure 17:
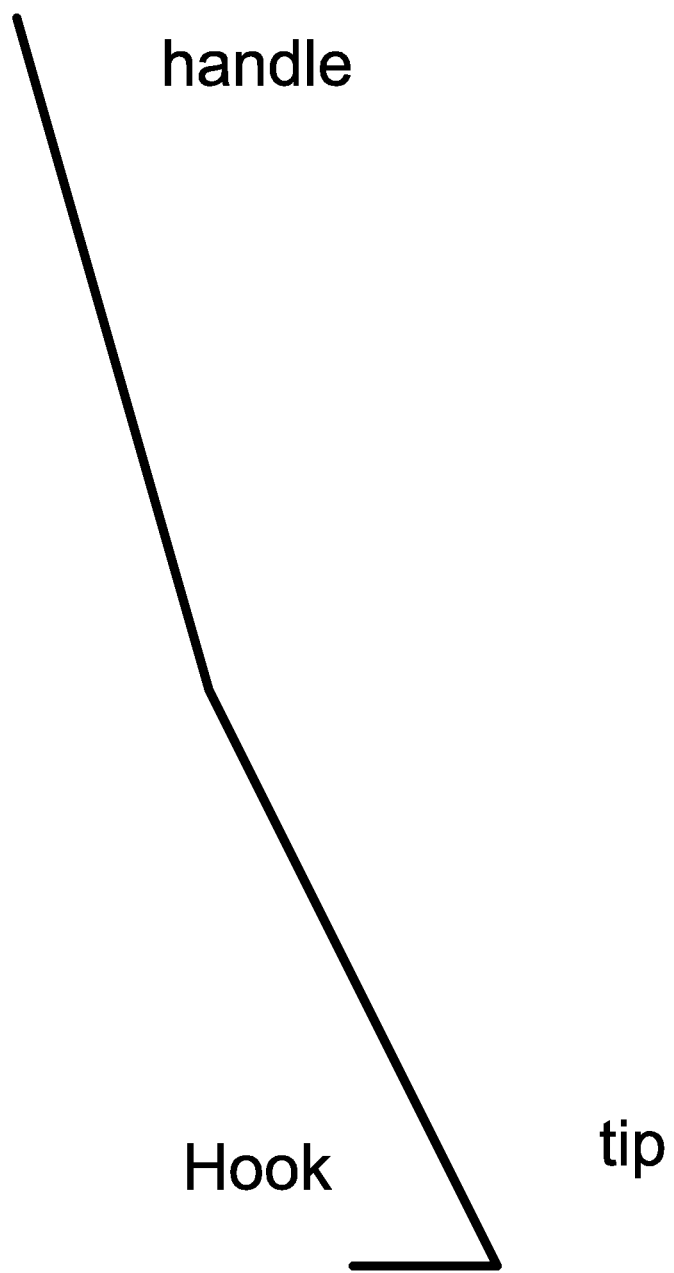
FIG. 17 is for one embodiment, as an example, for installation tool, e.g., to install or attach the ring or half-rings.

FIG. 17 is for one embodiment, as an example, for installation tool, e.g., to install or attach the ring or half-rings, with a single handle and shaft, with hook or extension at the tip for grabbing or directing the ring or equivalents, or to close, secure, lock, attach, or install the ring or equivalents.

Figure 18:
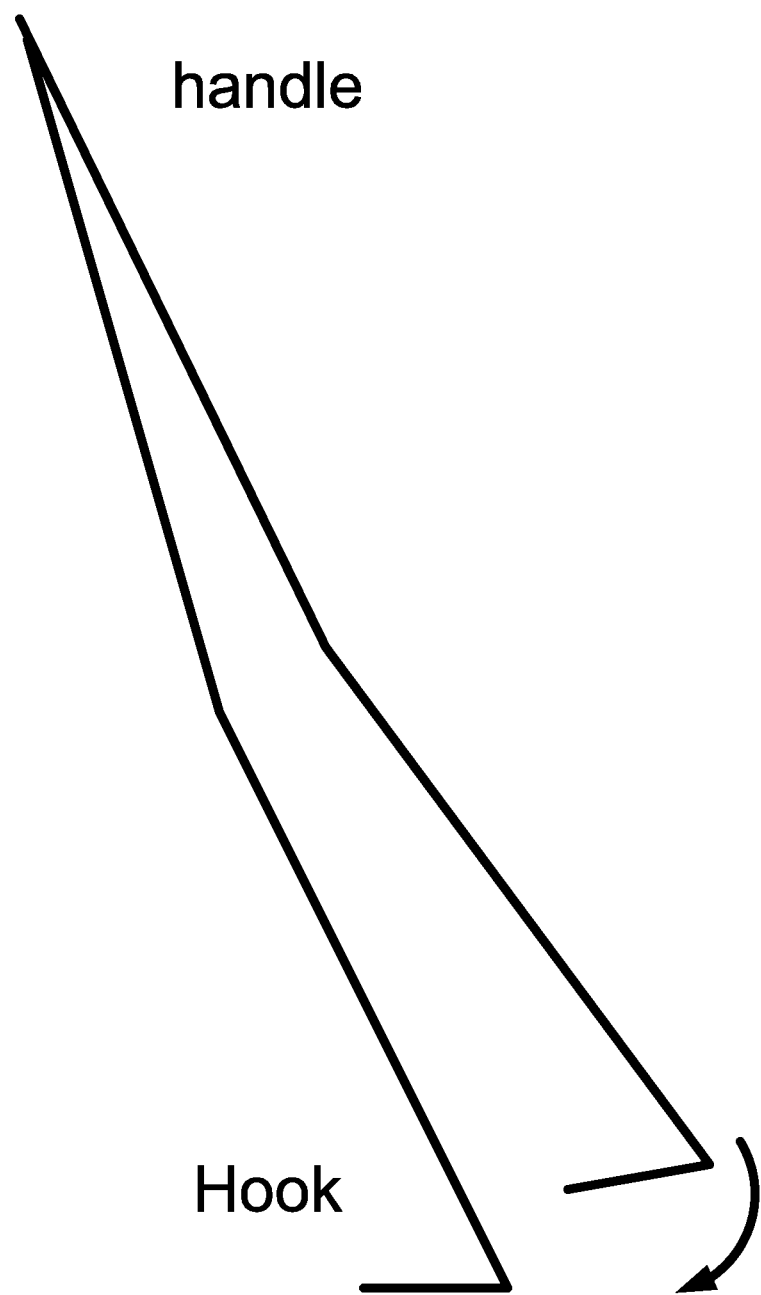
FIG. 18 is for one embodiment, as an example, for installation tool, e.g., to install or attach the ring or half-rings.
Figure 19:
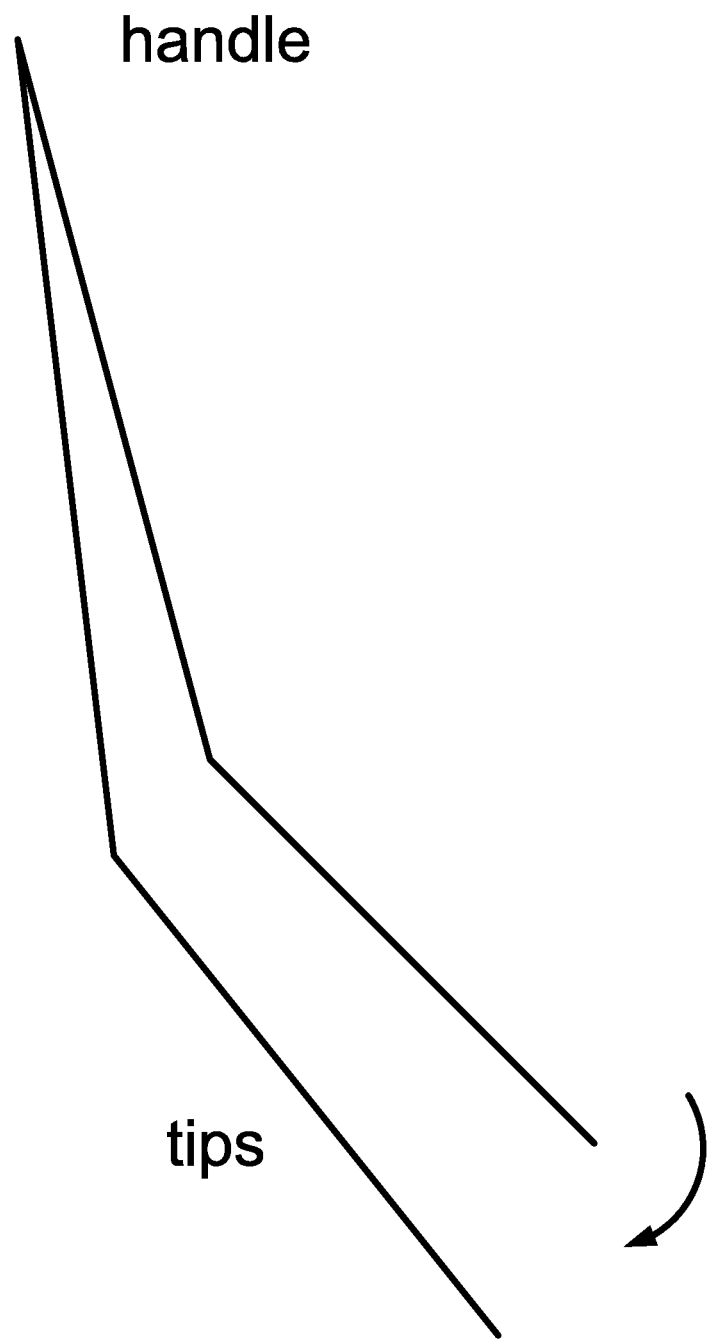
FIG. 19 is for one embodiment, as an example, for installation tool, e.g., to install or attach the ring or half-rings.

FIG. 18 is for one embodiment, as an example, for installation tool, e.g., to install or attach the ring or half-rings, as tweezers-like with 2 arms and one common handle on top, with spring action separating the arms in a normal condition, with fingers controlling the tips from the handle on top, with hooks at the tips, to direct and install the ring or equivalents. FIG. 19 is for one embodiment, as an example, for installation tool, e.g., to install or attach the ring or half-rings, similar to FIG. 18, but without the hooks at the tips, as a variation of the above.

Figure 20:
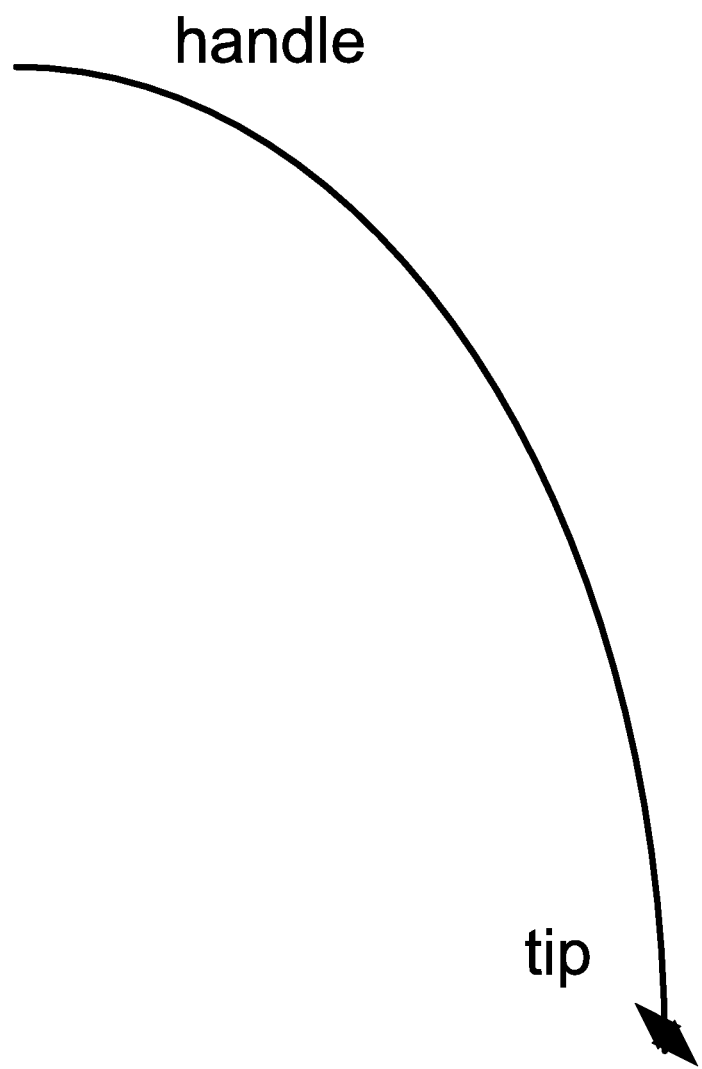
FIG. 20 is for one embodiment, as an example, for installation tool, e.g., to install or attach the ring or half-rings.
Figure 21:
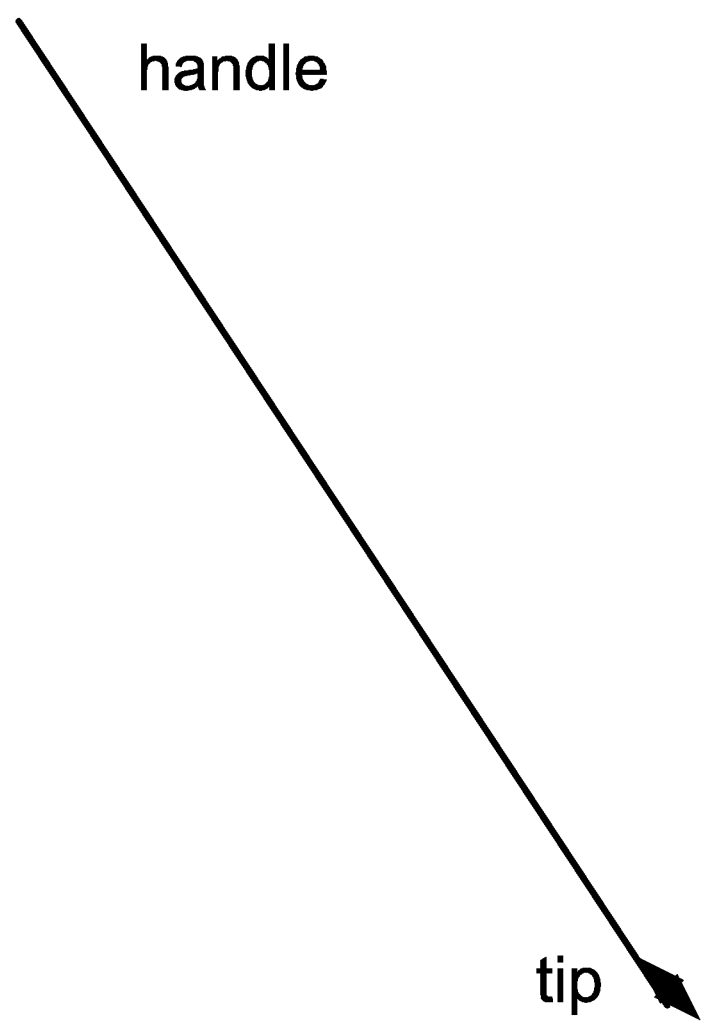
FIG. 21 is for one embodiment, as an example, for installation tool, e.g., to install or attach the ring or half-rings.

FIG. 20 is for one embodiment, as an example, for installation tool, e.g., to install or attach the ring or half-rings, using a single handle and tip, as diamond or arrow head, and in some embodiments, with a curved handle (for better maneuverability). FIG. 21 is for one embodiment, as an example, for installation tool, e.g., to install or attach the ring or half-rings, with straight handle in one example.

Figure 22:
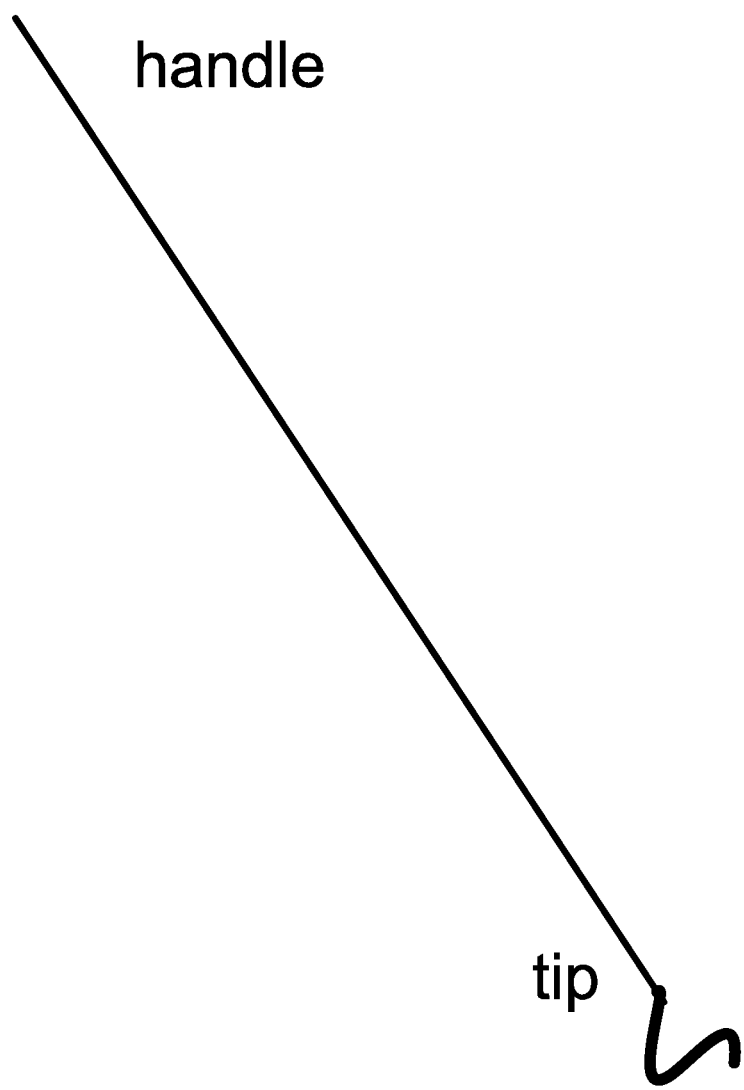
FIG. 22 is for one embodiment, as an example, for installation tool, e.g., to install or attach the ring or half-rings.
Figure 23:
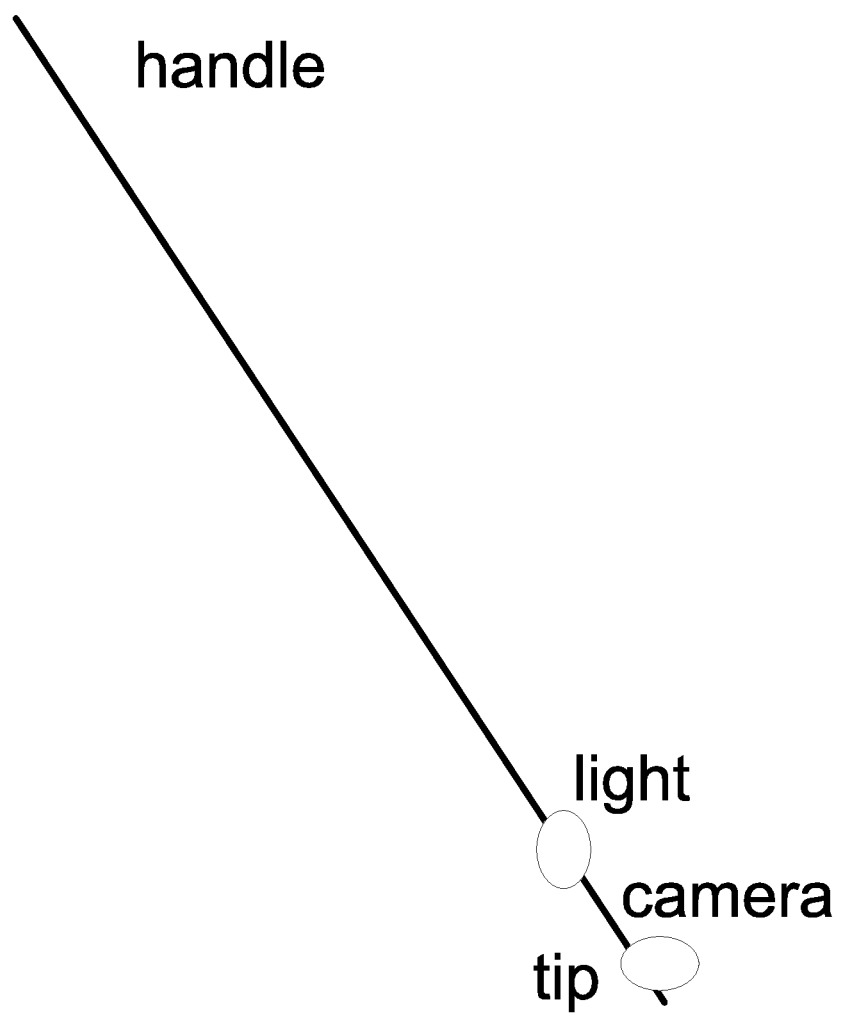
FIG. 23 is for one embodiment, as an example, for a tool with a light and camera for inspection during surgery.
Figure 24:
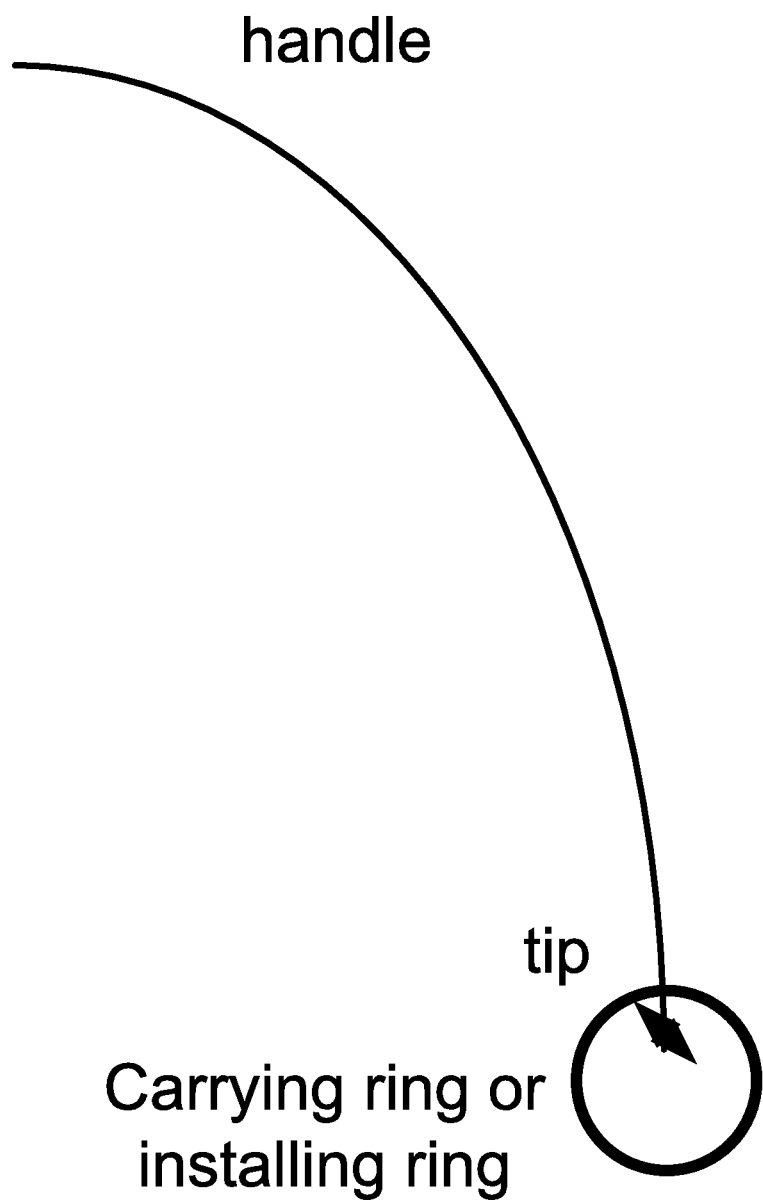
FIG. 24 is for one embodiment, as an example, for installation tool, e.g., to install or attach the ring or half-rings.

FIG. 22 is for one embodiment, as an example, for installation tool, e.g., to install or attach the ring or half-rings, using a hook or wiggly tip. FIG. 23 is for one embodiment, as an example, for a tool with a light and camera for inspection during surgery. FIG. 24 is for one embodiment, as an example, for installation tool, e.g., to install or attach the ring or half-rings, using the tip to carry or install or attach.

Figure 25:
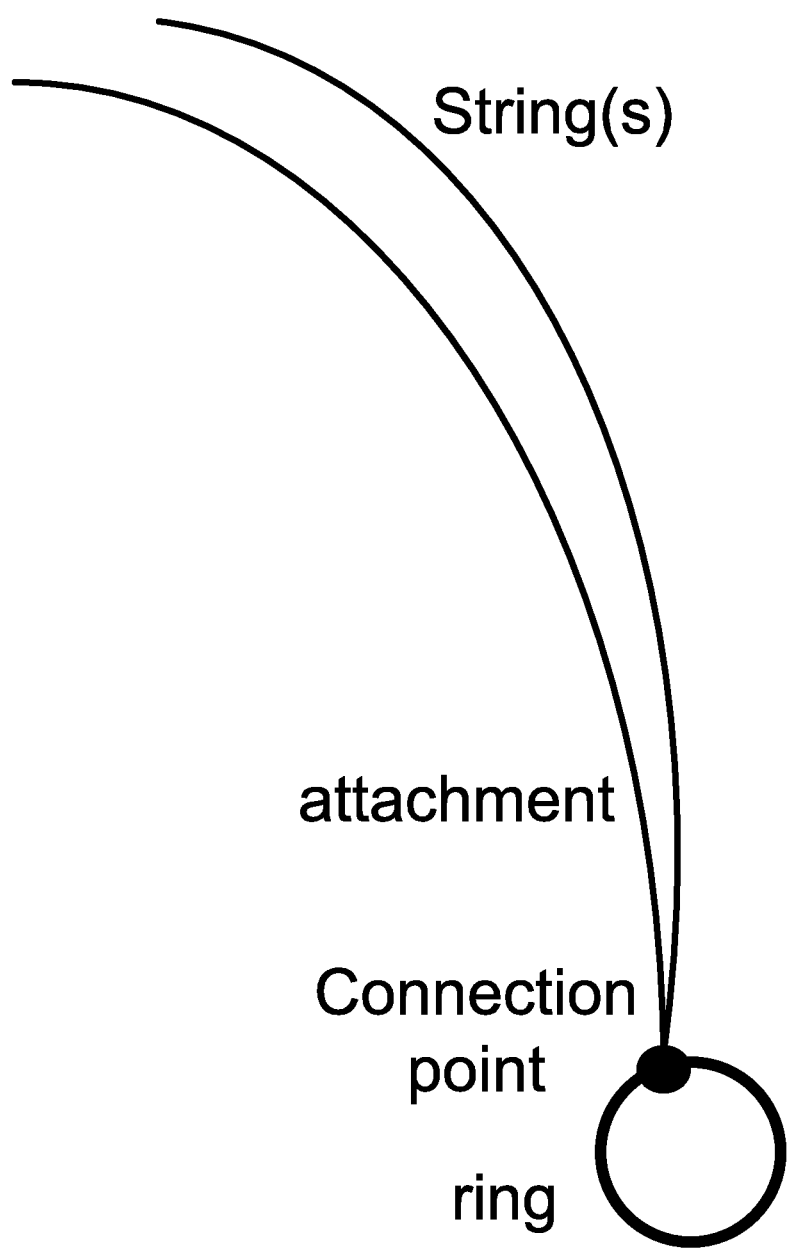
FIG. 25 is for one embodiment, as an example, for ring with one or more strings, with one or more connection points, or a knot or any glue or adhesive material.
Figure 26:
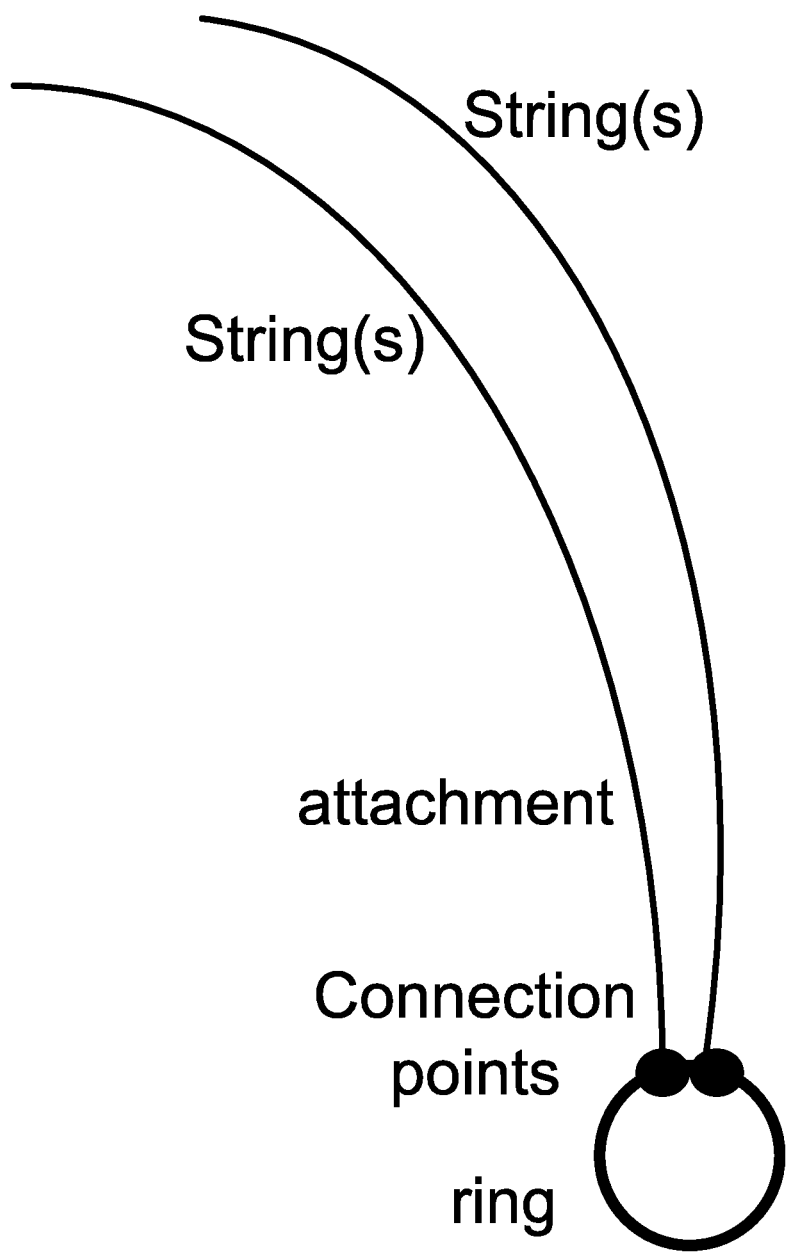
FIG. 26 is for one embodiment, as an example, for ring with one or more strings, with multiple connection points, or a knot or any glue or adhesive material.

FIG. 25 is for one embodiment, as an example, for ring with one or more strings, with one or more connection points, or a knot or any glue or adhesive material, with one or more strings per connection point, as attachment on the ring, to connect the components on the heart, as described elsewhere in this spec. FIG. 26 is for one embodiment, as an example, for ring with one or more strings, with multiple connection points, or a knot or any glue or adhesive material, which are positioned at different sides or various points on the ring, on the circumference of the circle or ring.

In one example, we have a ring, with the structure as spiral with spring-type loaded to stay flat on a plane, folding on itself multiple times, as multiple stacked circles on top of each other, on the same circle. This ring looks like the common key chain ring that people use for holding their keys. The ring can engage and connect the tissue and strings, as they go through the tight gaps on the ring between neighboring stacked circles, to stay in place with friction and pressure, using the spring-action on the ring vertically (vertical to the plane of the ring), to keep tissue and strings stable and in place, for position and location, with respect to the ring. So, everything stays in place and secure for the lower end of the connector for the heart. In one example, we have to rotate the ring in a direction to gradually engage tissue between the gaps between the stacks of rings or circles. The strings had already been engaged into the gaps between the stacks of rings or circles, from the factory, or by the surgeon before the surgery, to be ready for the surgery, as one embodiment.

Figure 27:
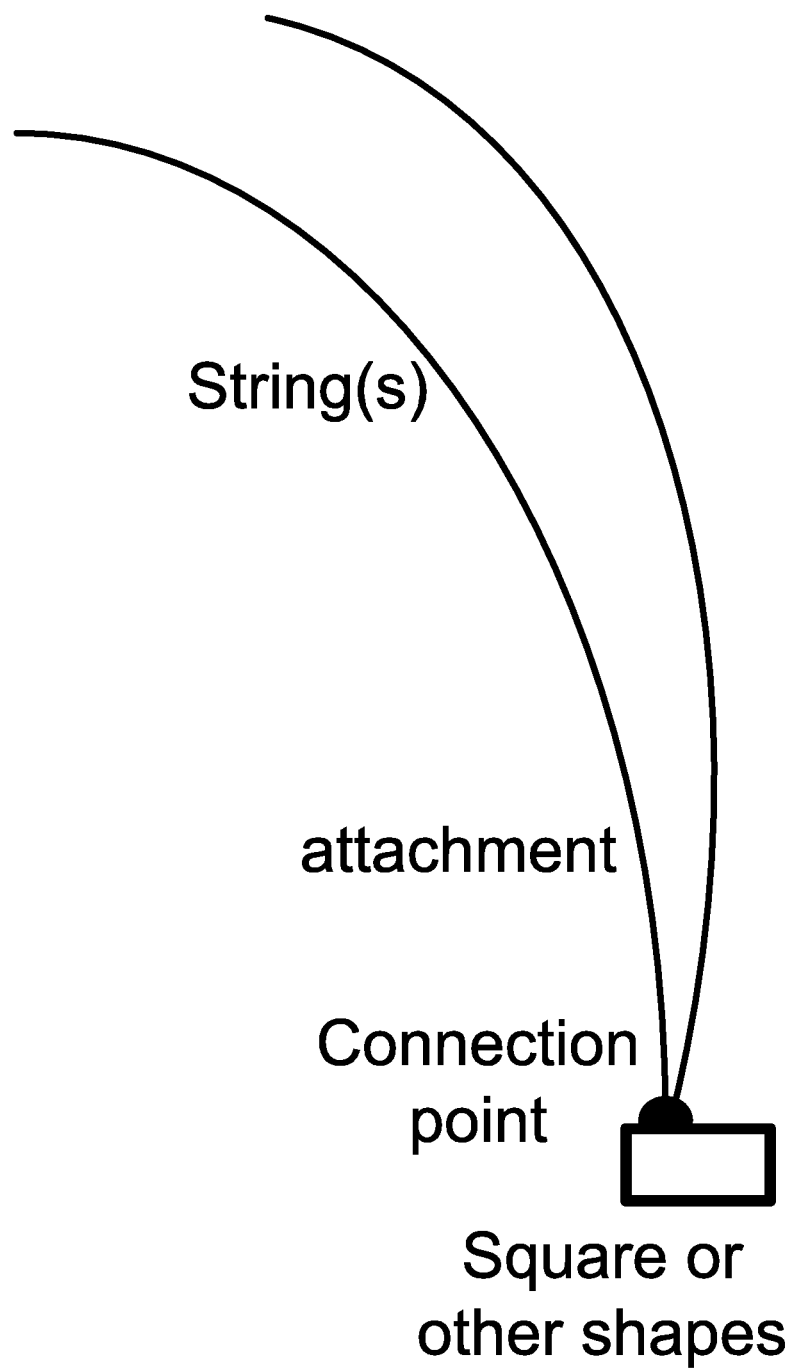
FIG. 27 is for one embodiment, as an example, for square or other shapes, with one or more strings, with connection point(s), or a knot or any glue or adhesive material.
Figure 28:
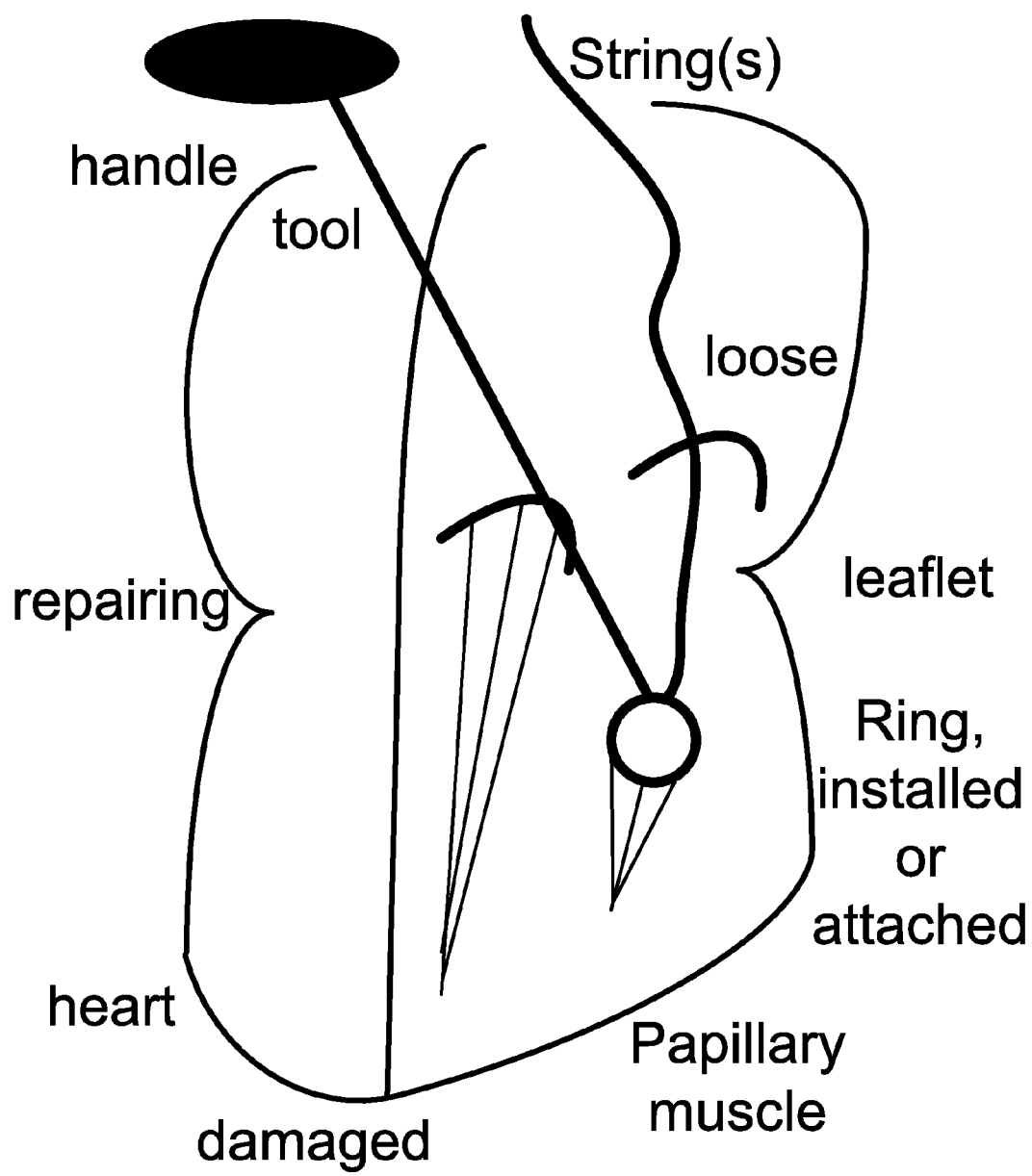
FIG. 28 is for one embodiment, as an example, for ring with one or more strings, with connection points, installed or attached by the installment tool, to repair the component of the heart, for the valve working properly.

FIG. 27 is for one embodiment, as an example, for square or other shapes, with one or more strings, with connection point(s), or a knot or any glue or adhesive material. FIG. 28 is for one embodiment, as an example, for ring or equivalent, with one or more strings, with connection points, installed or attached by the installment tool, to repair the component of the heart, for the valve working properly, going inside the heart using the installment tool, after the leaflet becomes loose and non-functional.

Figure 29:
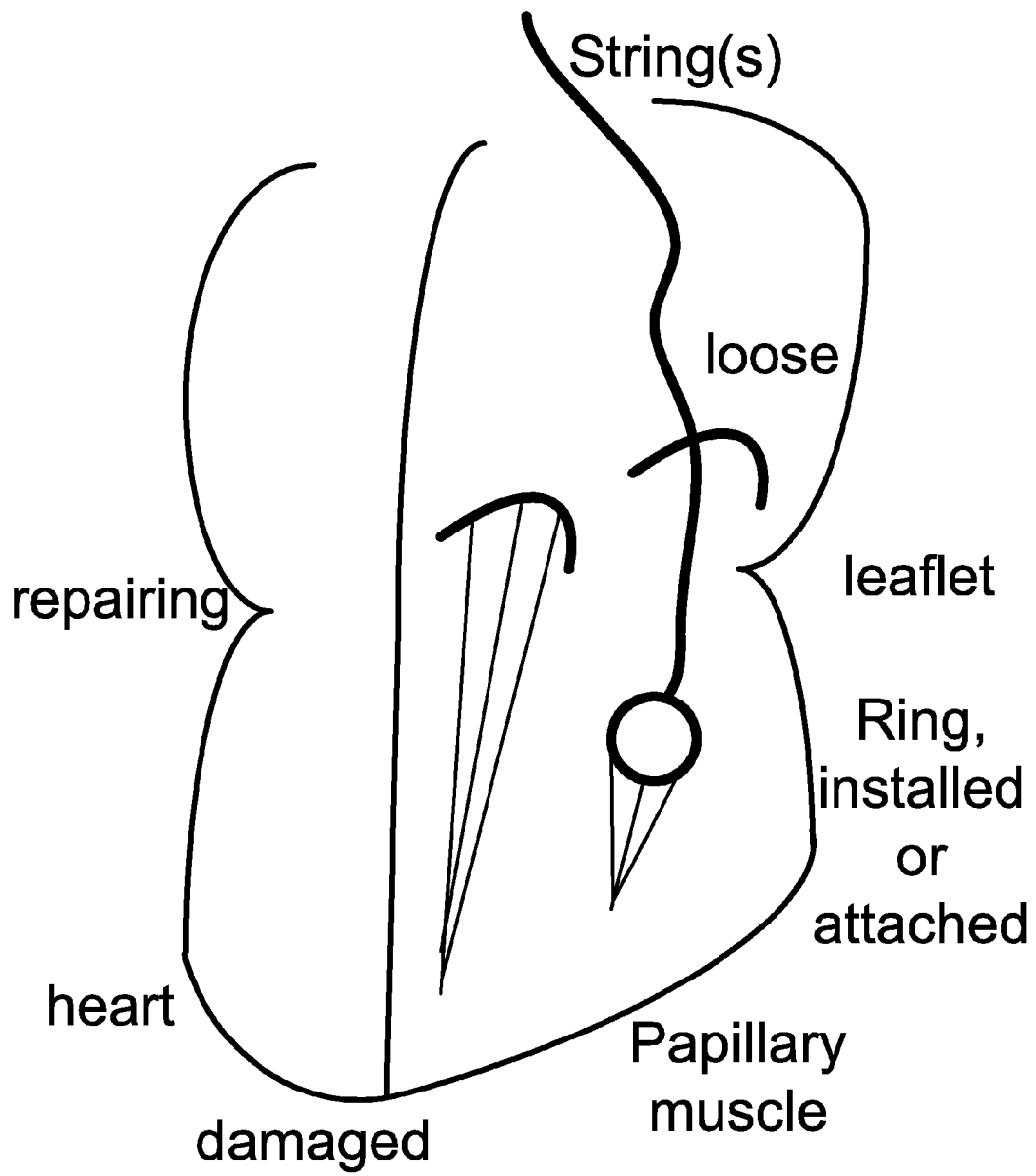
FIG. 29 is for one embodiment, as an example, for ring with one or more strings, with connection points, to repair the component of the heart, for the valve working properly.
Figure 30:
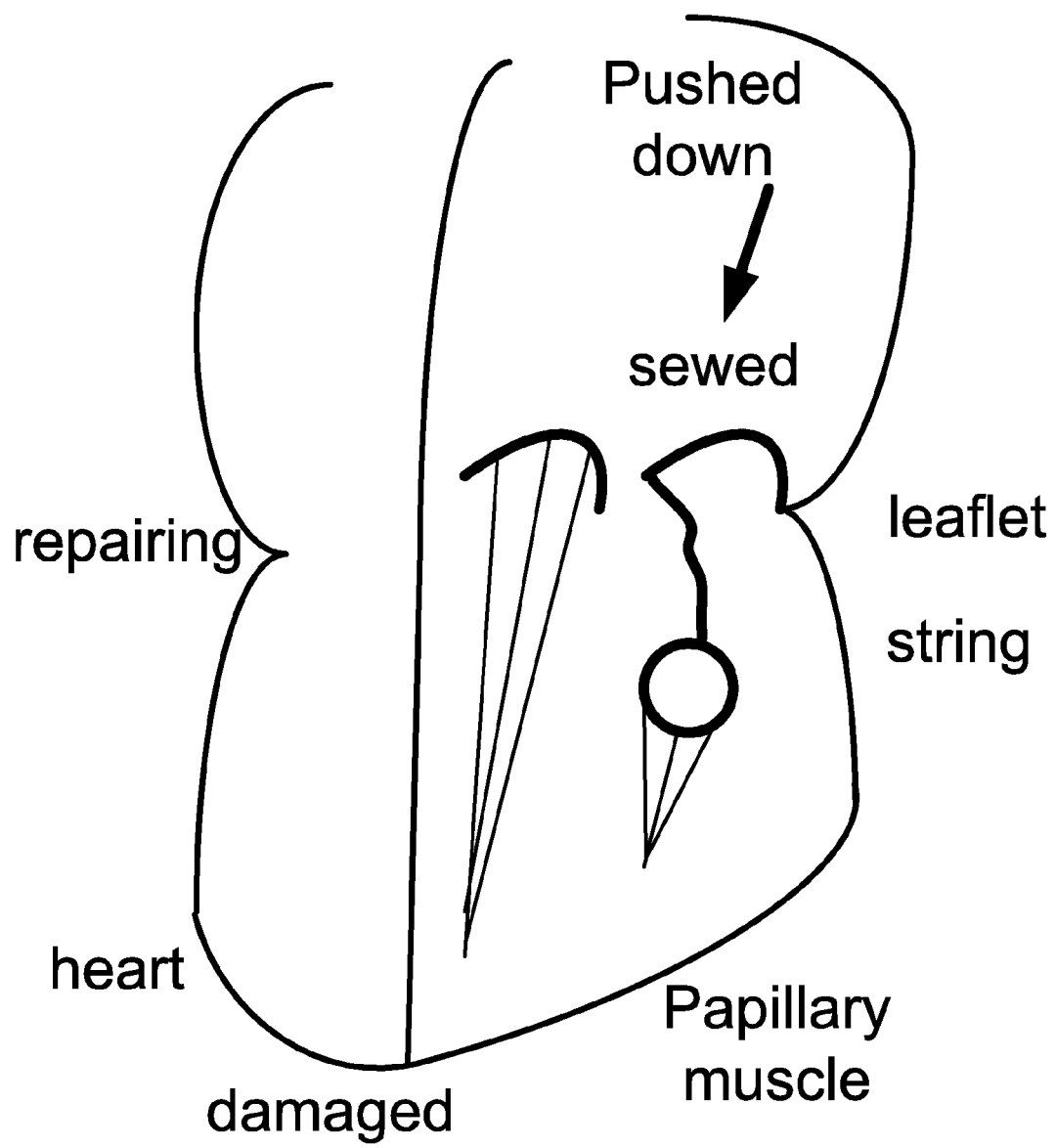
FIG. 30 is for one embodiment, as an example, for ring with one or more strings, with connection points, to repair the component of the heart, for the valve working properly, e.g., attached or sewed to the leaflet, to push that down, for proper position and functioning.

FIG. 29 is for one embodiment, as an example, for ring with one or more strings, with connection points, to repair the component of the heart, for the valve working properly, after the installment tool is taken out during surgery. FIG. 30 is for one embodiment, as an example, for ring with one or more strings, with connection points, to repair the component of the heart, for the valve working properly, e.g., with string(s) attached or sewed to the leaflet, to push that down, for proper position and functioning of the valve.

Figure 31:
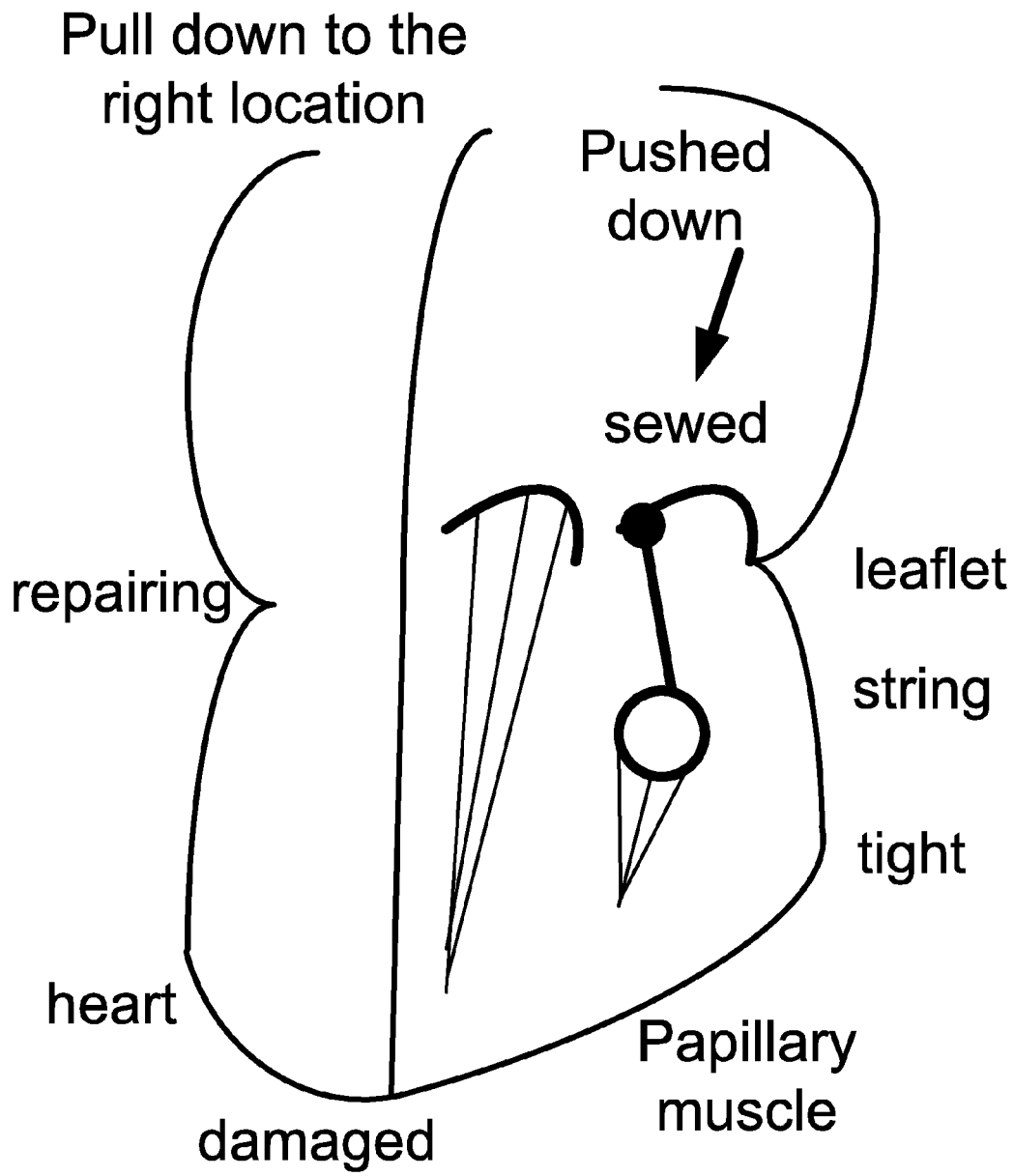
FIG. 31 is for one embodiment, as an example, for ring with one or more strings, with connection points, to repair the component of the heart, for the valve working properly, e.g., attached or sewed to the leaflet, to push that down, for proper position and functioning, repairing the valve.

FIG. 31 is for one embodiment, as an example, for ring with one or more strings, with connection points, to repair the component of the heart, for the valve working properly, e.g., with string(s) attached or sewed to the leaflet, to push that down, for proper position and functioning, repairing the valve, with a tight grip between valve and the ring.

Figure 32:
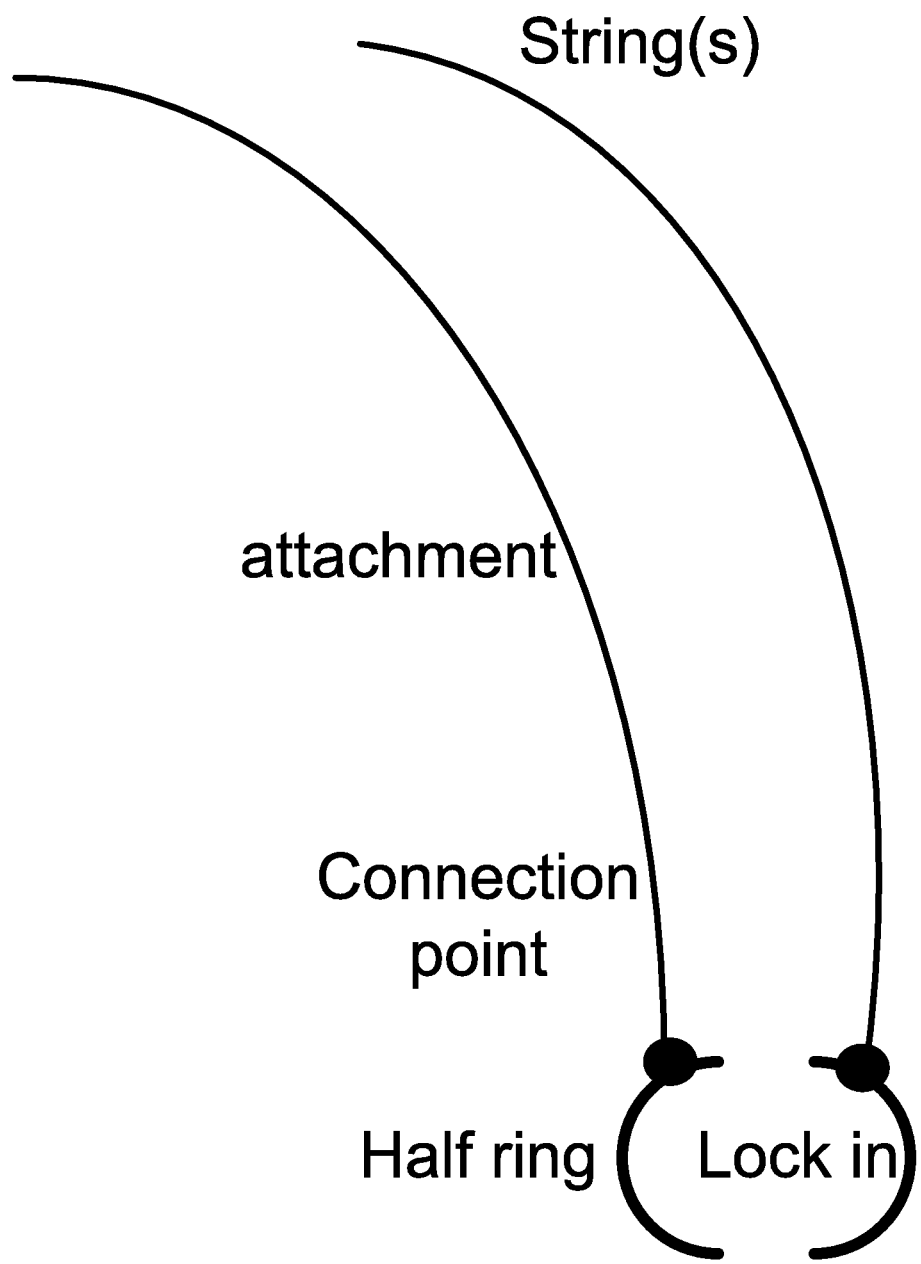
FIG. 32 is for one embodiment, as an example, for two half-rings with one or more strings for each, with connection points, to lock in or fit into each other, as a complete ring, or full circle, for attachment, for bottom part of the heart.
Figure 33:
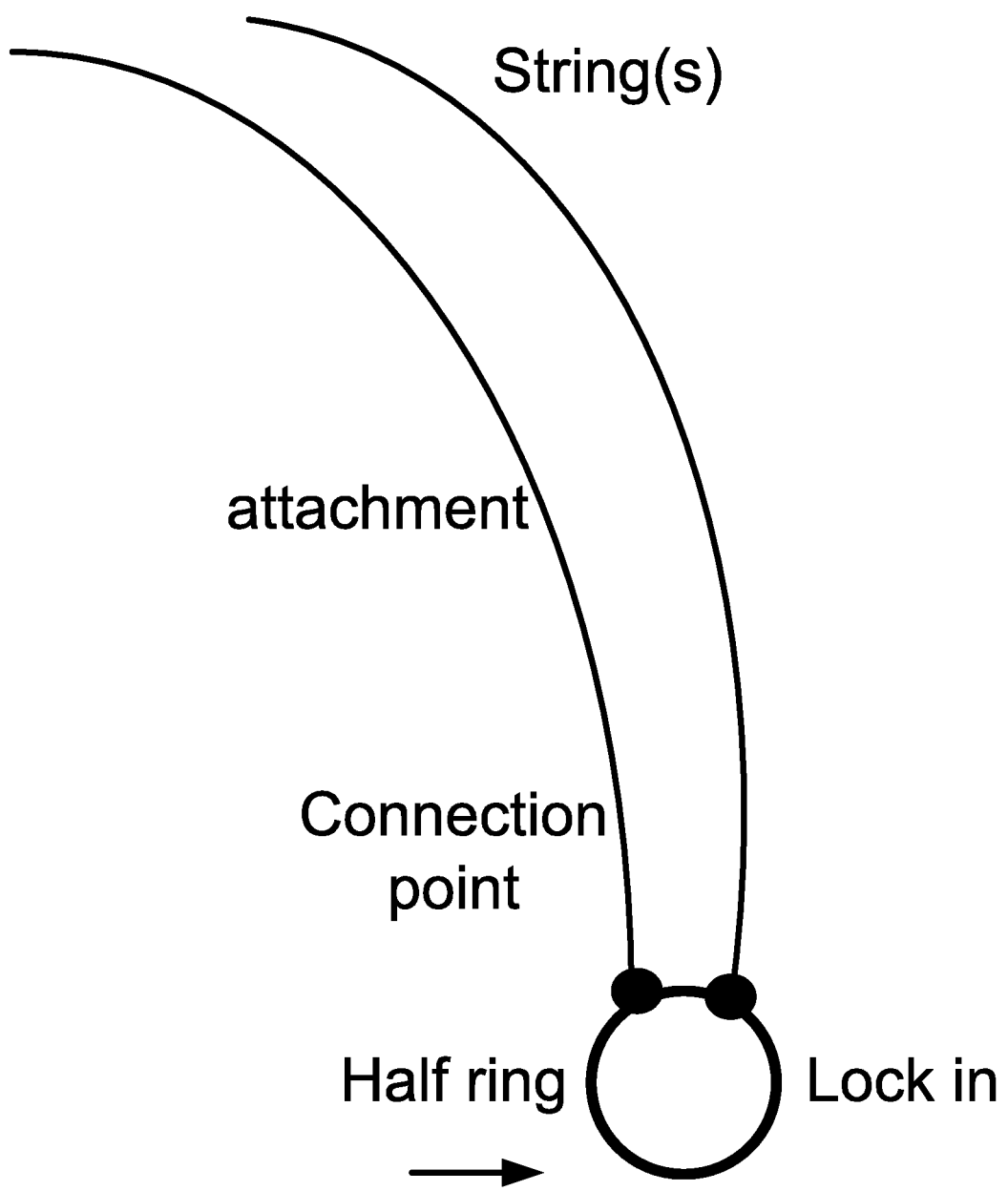
FIG. 33 is for one embodiment, as an example, for two half-rings with one or more strings for each, with connection points, to lock in or fit into each other, pushed in to click or engage, as a complete ring, or full circle, for attachment, for bottom part of the heart.

FIG. 32 is for one embodiment, as an example, for two half-rings with one or more strings for each, with connection points, to lock in or fit into each other, as a complete ring, or full circle, for attachment, for bottom part of the heart. FIG. 33 is for one embodiment, as an example, for two half-rings with one or more strings for each, with connection points, to lock in or fit into each other, pushed in to click or engage, as a complete ring, or full circle, for attachment, for bottom part of the heart, which is locked in with stability and durability.

Figure 34:
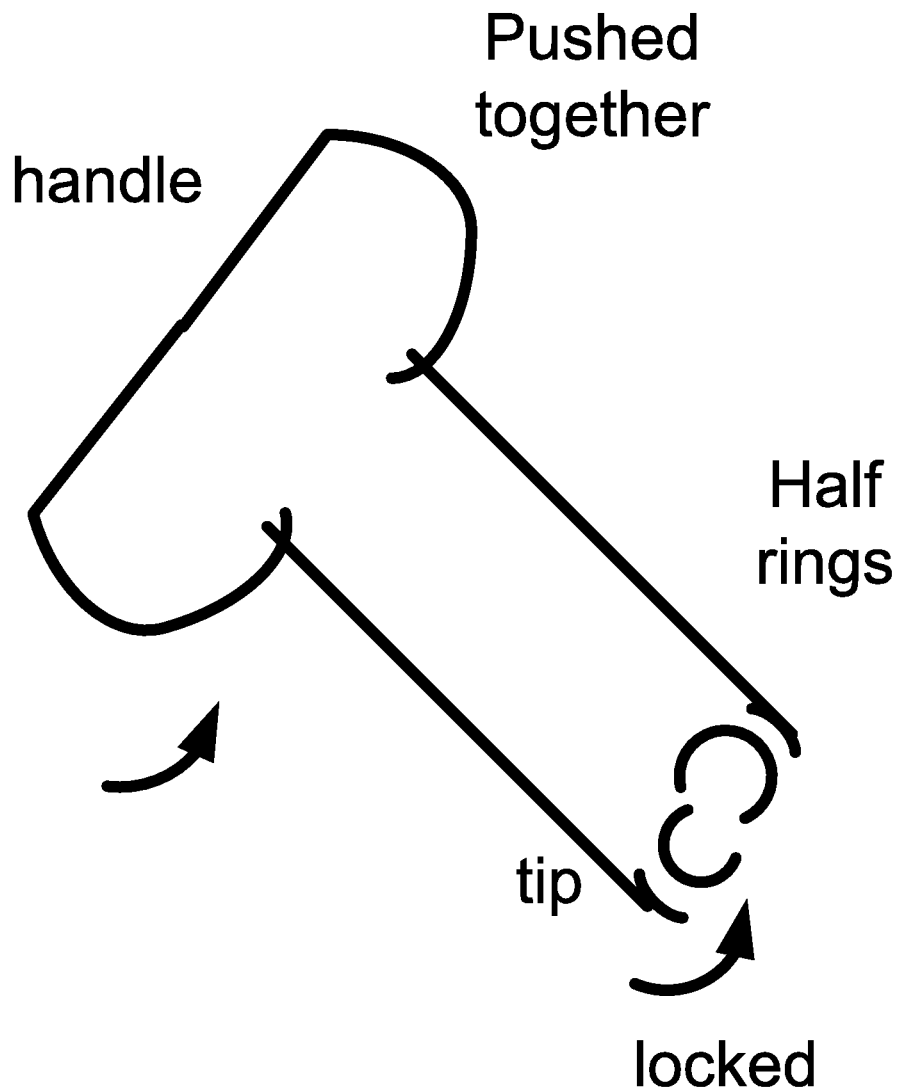
FIG. 34 is for one embodiment, as an example, for the installment tool, with two half-rings, to lock in or fit into each other, pushed in to click or engage, as a complete ring, or full circle, for attachment, for bottom part of the heart.

FIG. 34 is for one embodiment, as an example, for the installment tool, with two half-rings, to lock in or fit into each other, pushed in to click or engage, as a complete ring, or full circle, for attachment, for bottom part of the heart. The handle is adjusting the tips and applies pressure to the 2 arms, using the hand of the surgeon. The cups at the tip direct the pressure to the 2 half-rings, for more control and precision.

Figure 35:
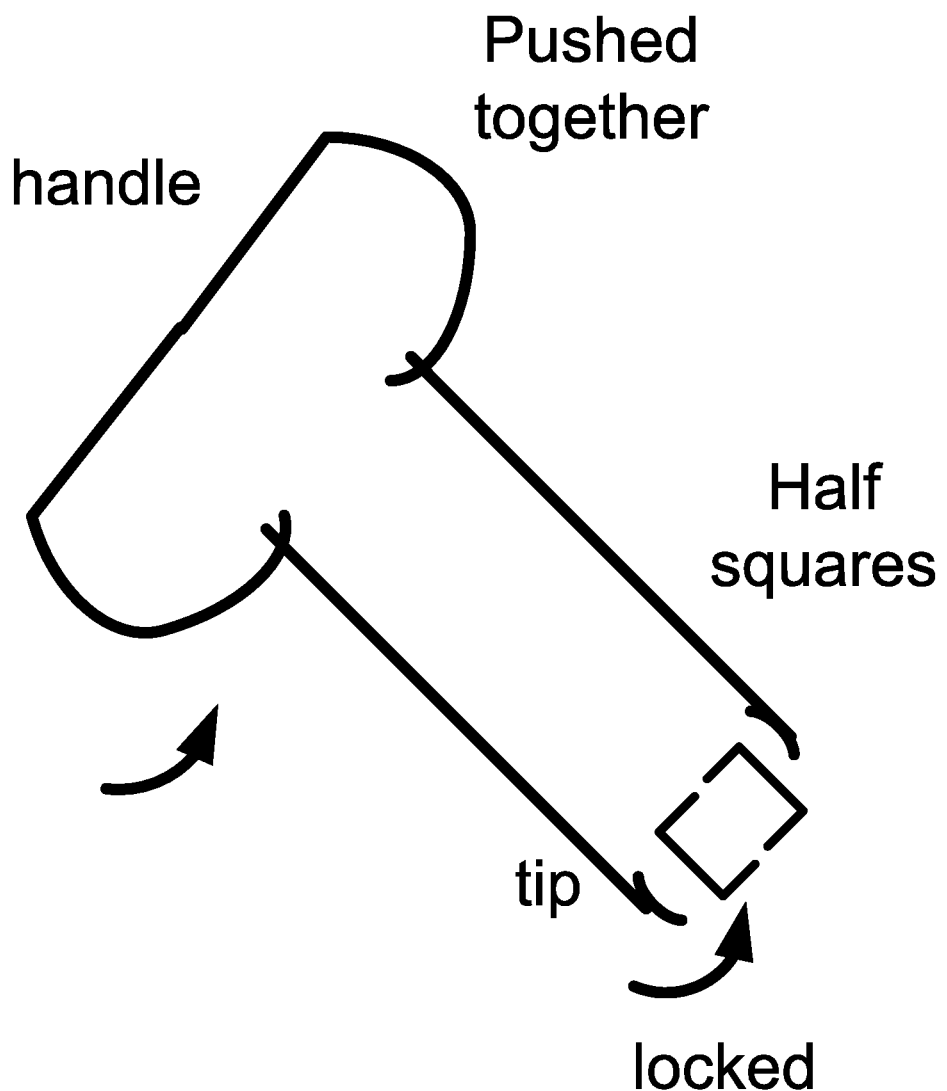
FIG. 35 is for one embodiment, as an example, for the installment tool, with two half-squares or rectangles, to lock in or fit into each other, pushed in to click or engage, as a complete square or rectangle, for attachment, for bottom part of the heart.

FIG. 35 is for one embodiment, as an example, for the installment tool, with two half-squares or rectangles, to lock in or fit into each other, pushed in to click or engage, as a complete square or rectangle, for attachment, for bottom part of the heart, very similar to functionalities described in FIG. 34, above.

Figure 1:
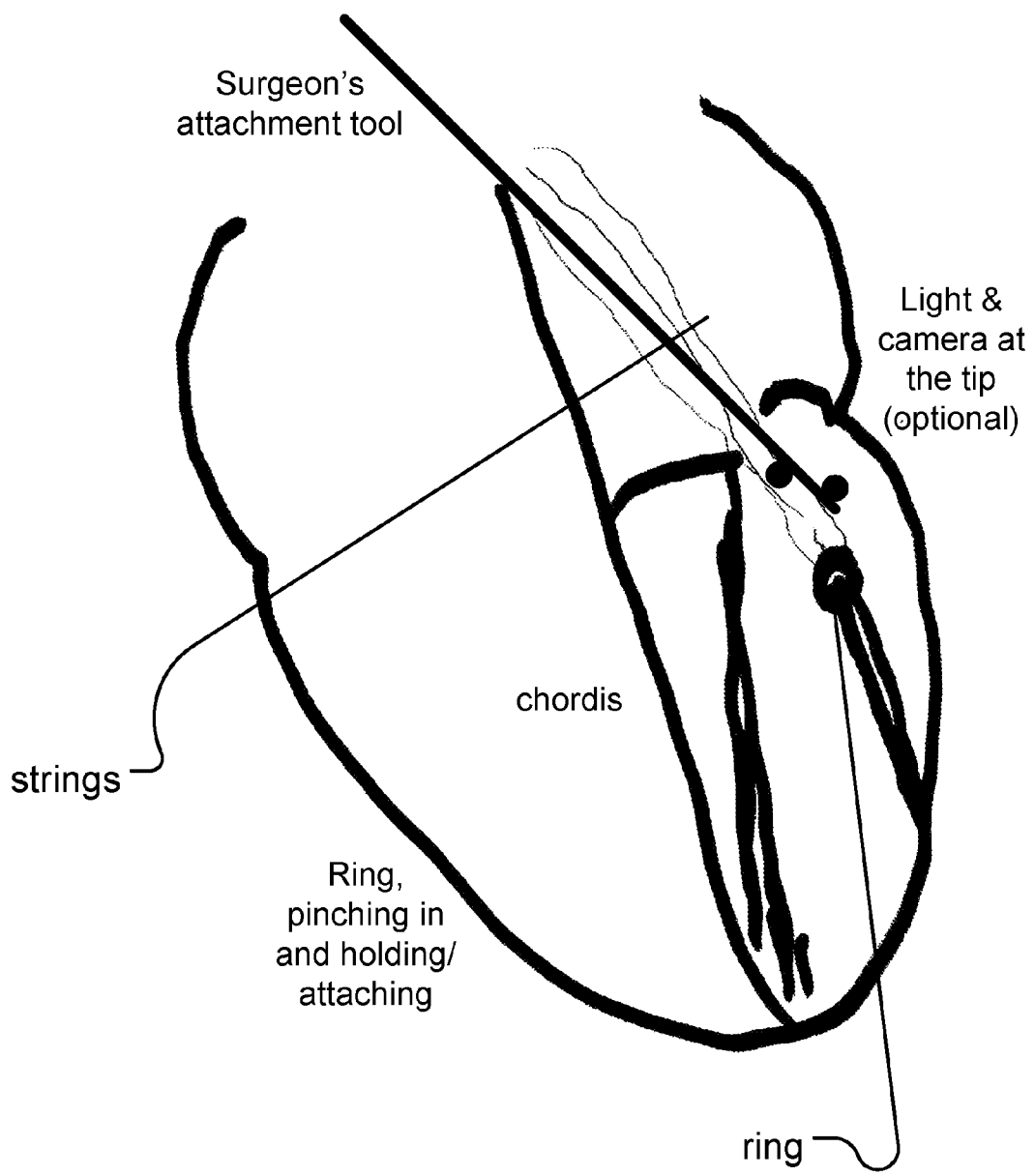
FIG. 1 is for one embodiment, as an example, for repairing heart components, using a ring attached to one or more strings, with ring attached or affixed to the bottom portion, inside the heart.

FIG. 1 is for one embodiment, as an example, for repairing heart components, using a ring attached to one or more strings, with ring attached or affixed to the bottom portion, inside the heart.

Figure 2:
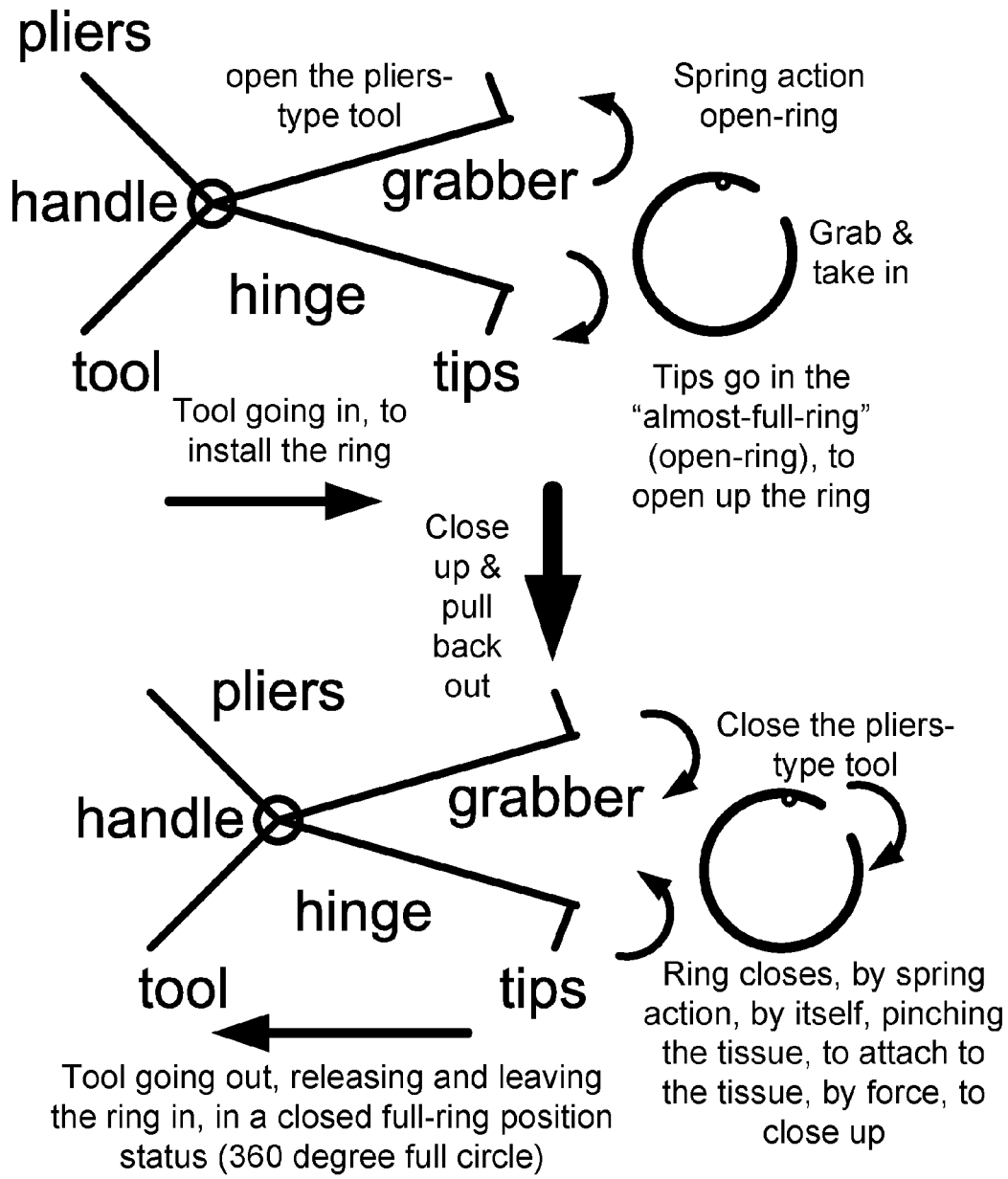
FIG. 2 is for one embodiment, as an example, for the tool or installer device for repairing heart components, using a ring attached to one or more strings, with ring attached or affixed to the bottom portion, inside the heart, at various stages of the operation for the tool or installer device.

FIG. 2 is for one embodiment, as an example, for the tool or installer device for repairing heart components, using a ring attached to one or more strings, with ring attached or affixed to the bottom portion, inside the heart, at various stages of the operation for the tool or installer device.

Figure 38:
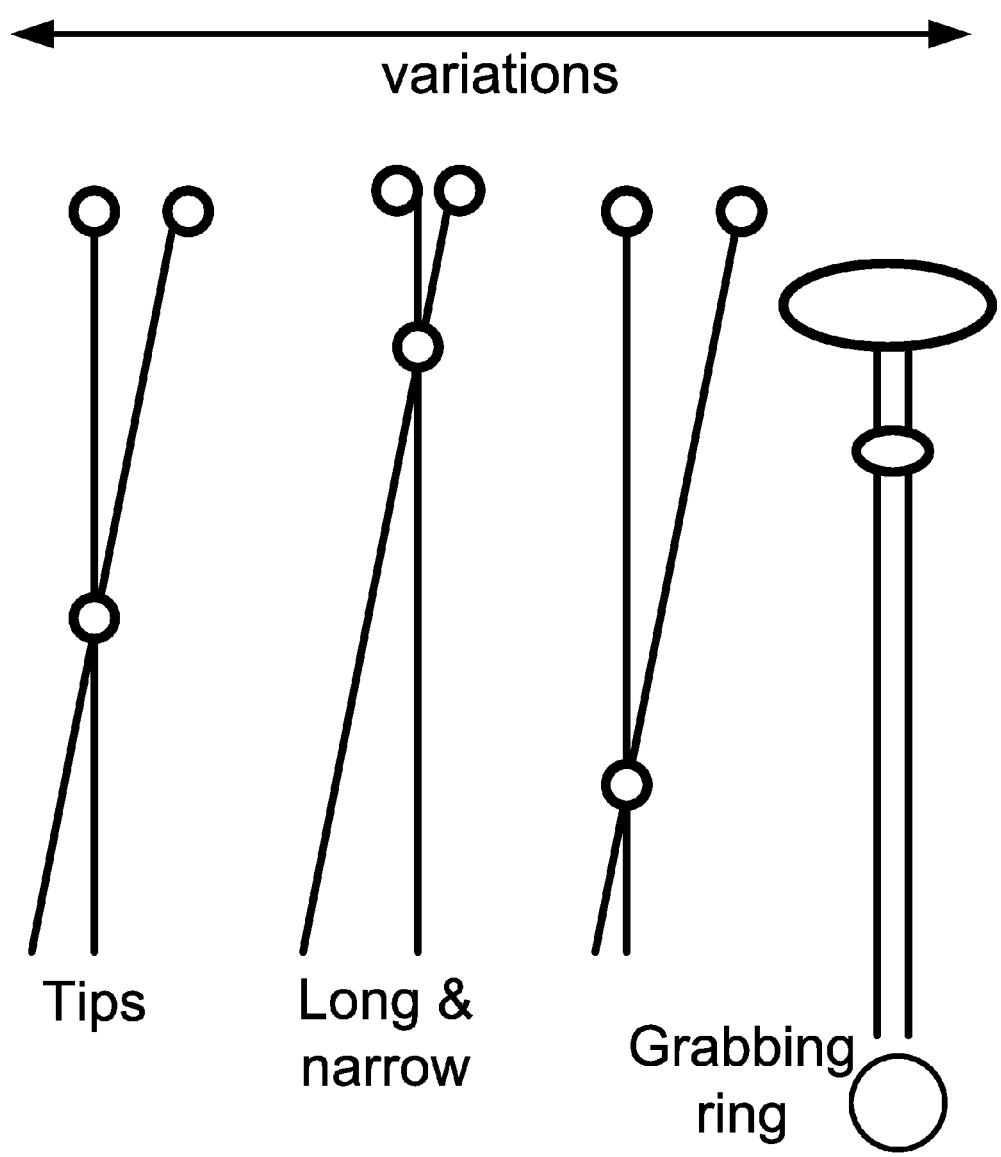
FIG. 38 is for one embodiment, as an example, for the installment tool, with variations of the structure.
Figure 39:
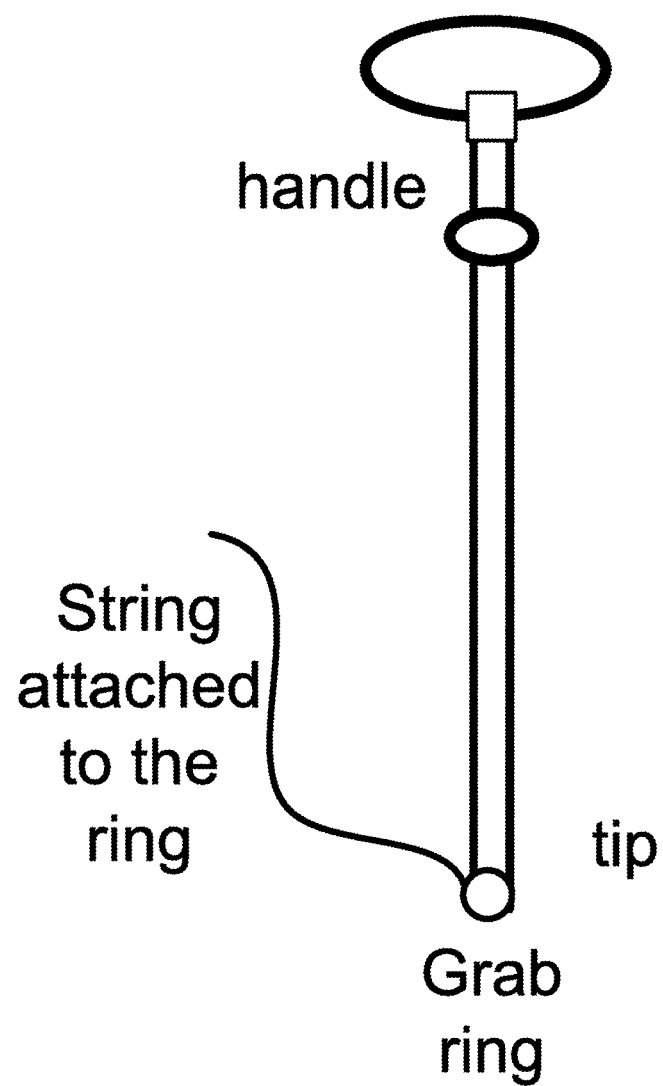
FIG. 39 is for one embodiment, as an example, for the installment tool.
Figure 40:
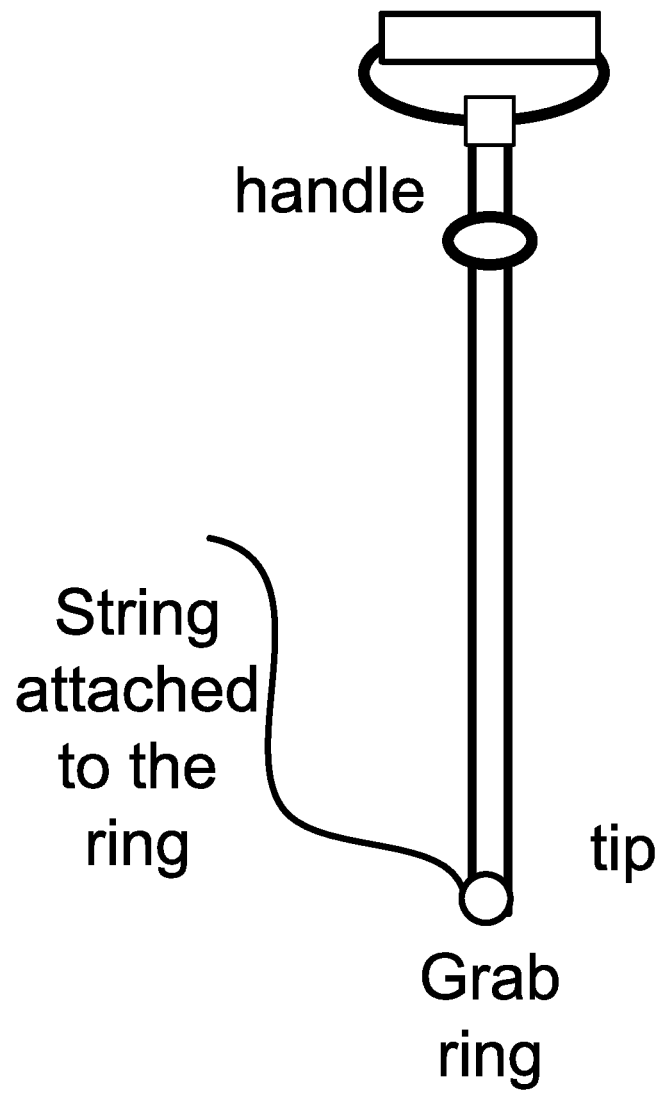
FIG. 40 is for one embodiment, as an example, for the installment tool.
Figure 41:
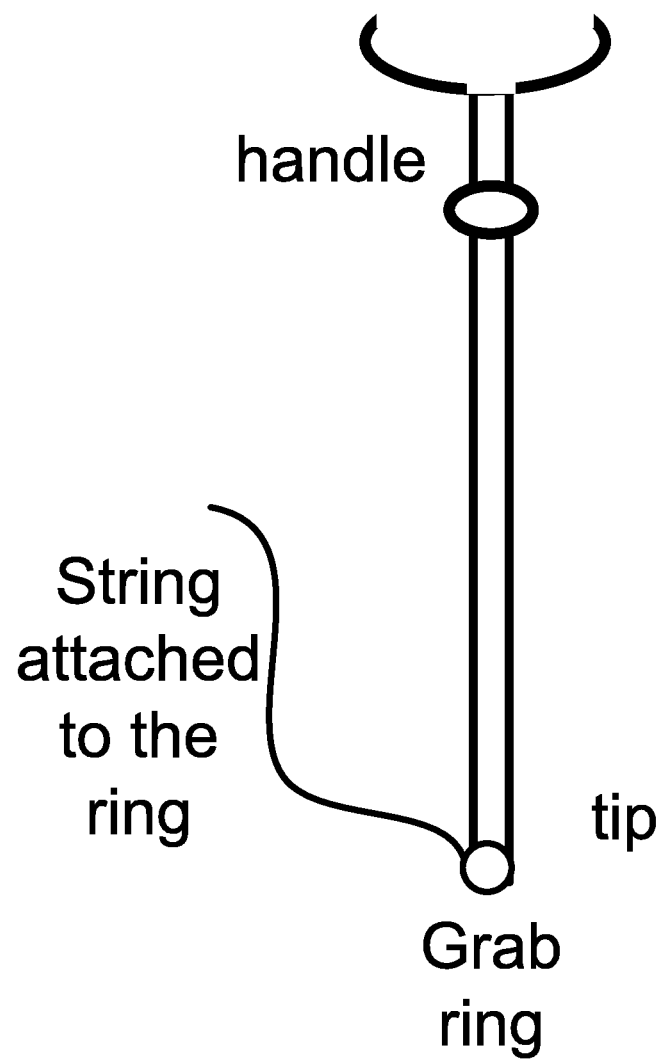
FIG. 41 is for one embodiment, as an example, for the installment tool.
Figure 42:
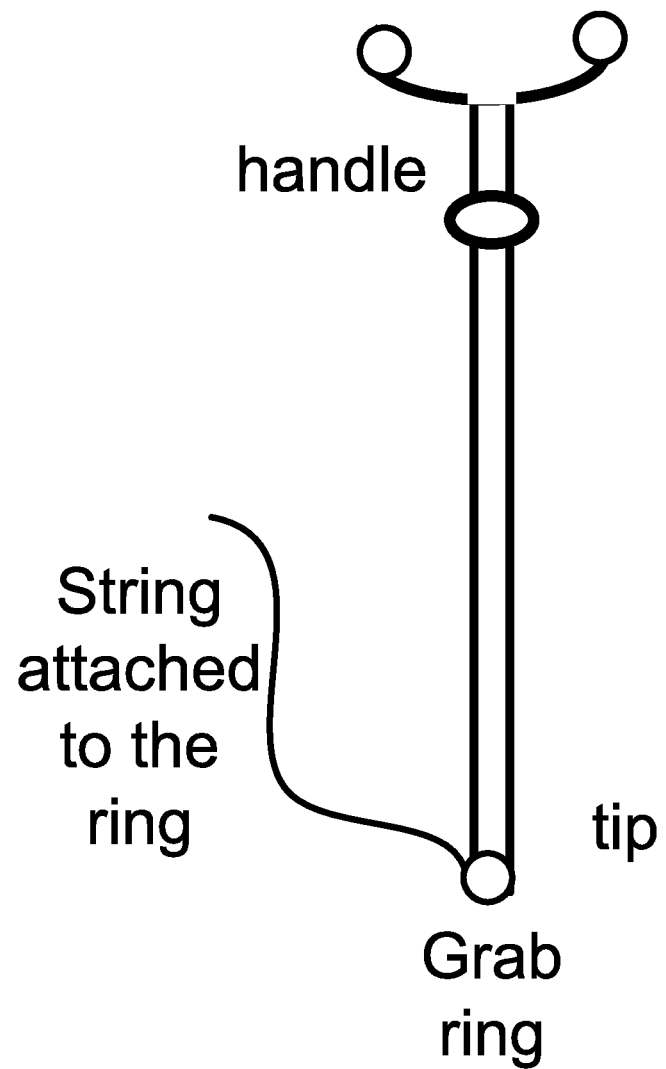
FIG. 42 is for one embodiment, as an example, for the installment tool.
Figure 43:
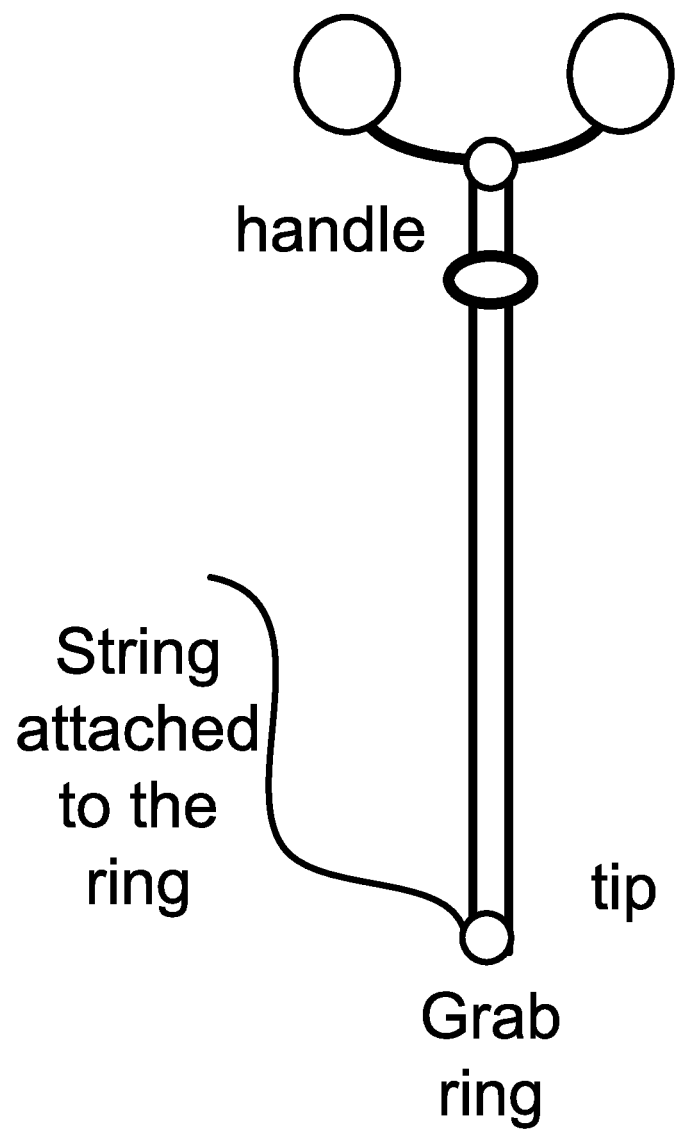
FIG. 43 is for one embodiment, as an example, for the installment tool.
Figure 44:
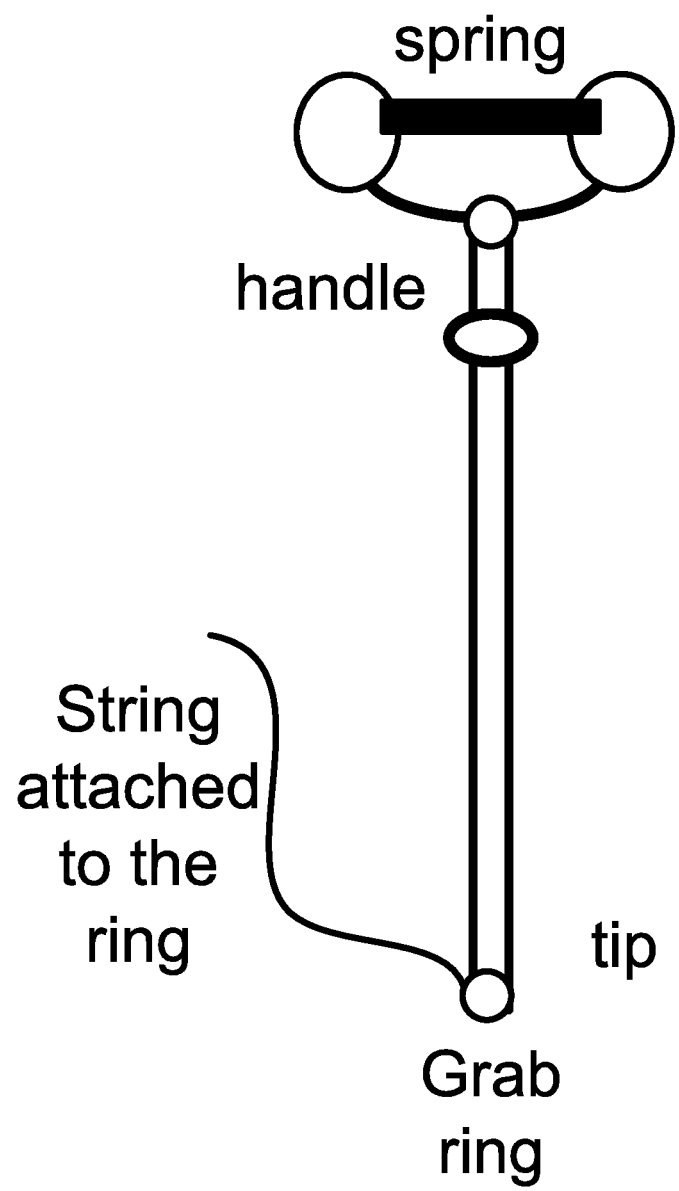
FIG. 44 is for one embodiment, as an example, for the installment tool.
Figure 45:
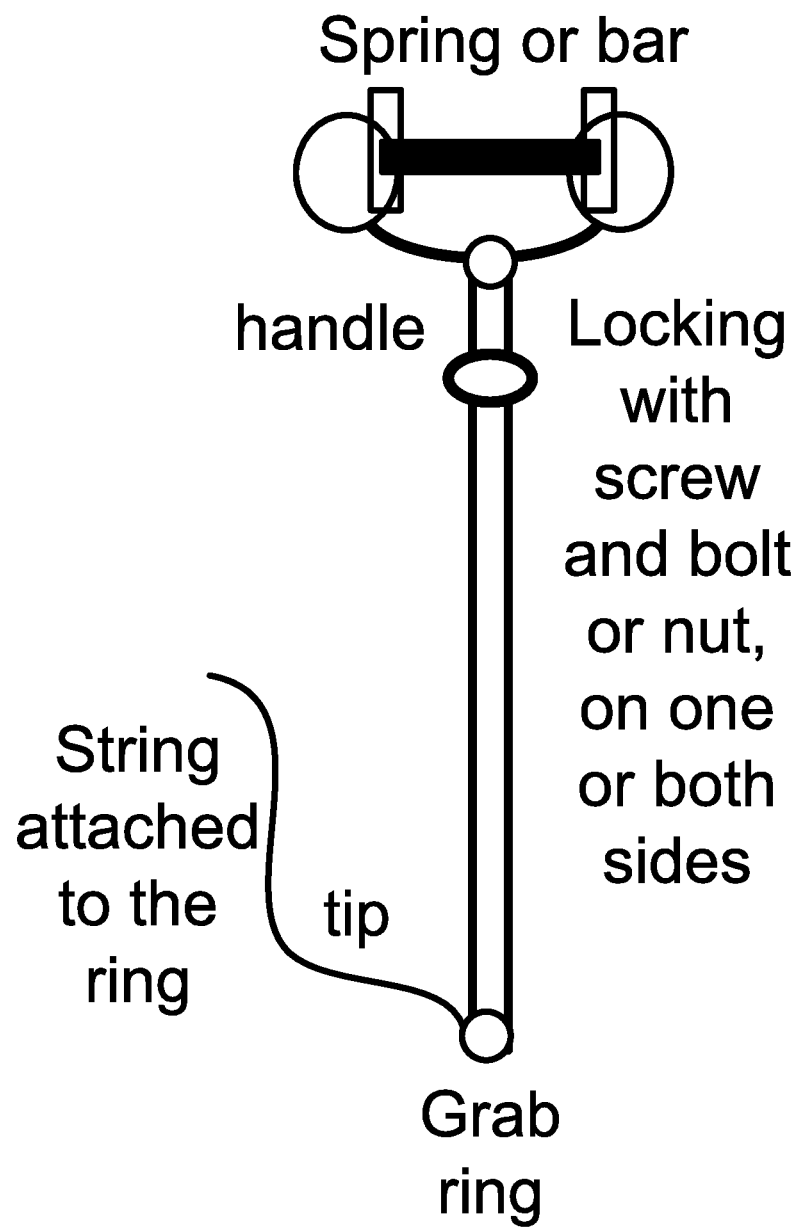
FIG. 45 is for one embodiment, as an example, for the installment tool.
Figure 46:
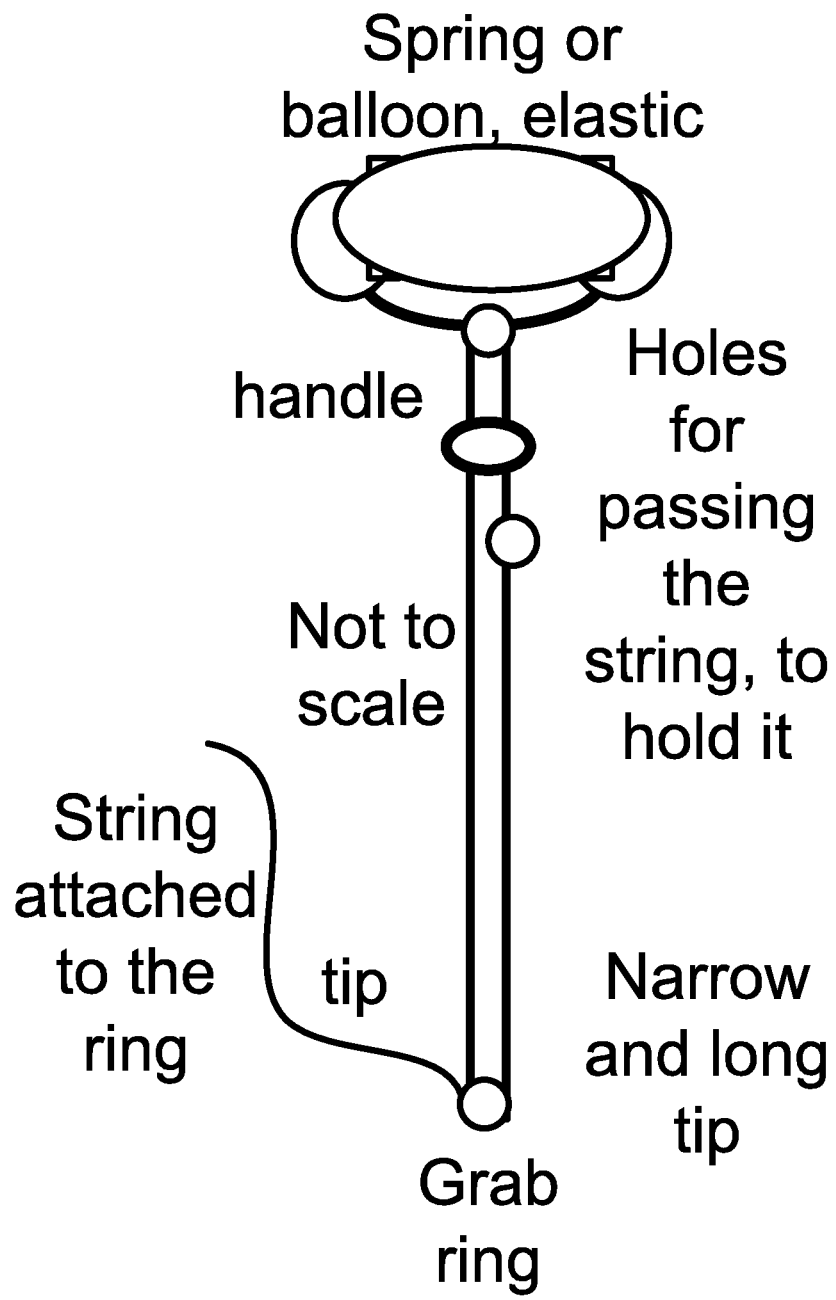
FIG. 46 is for one embodiment, as an example, for the installment tool.

FIG. 38 is for one embodiment, as an example, for the installment tool, with variations of the structure. FIG. 39 is for one embodiment, as an example, for the installment tool. FIG. 40 is for one embodiment, as an example, for the installment tool. FIG. 41 is for one embodiment, as an example, for the installment tool. FIG. 42 is for one embodiment, as an example, for the installment tool. FIG. 43 is for one embodiment, as an example, for the installment tool. FIG. 44 is for one embodiment, as an example, for the installment tool. FIG. 45 is for one embodiment, as an example, for the installment tool. FIG. 46 is for one embodiment, as an example, for the installment tool.

In one example, we use 2-4 strings per ring. In one example, the top portion of the heart component is sewed or stitched or sutured, and the rest of string on the length (extra length) is cut and thrown out. In one example, the string or suture material, for new chorde, is based on plastic or other artificial or natural materials commonly used for surgery or medical applications, or known to the industry.

Any variations of the above teaching are also intended to be covered by this patent application.

The invention claimed is:

1. An apparatus system for heart surgery, said apparatus system comprising:
   an installer device;
   a first full-circle-ring attached to a first set of one or more strings;
   wherein said full-circle-ring has a cut in its circumference;
   wherein said first full-circle-ring has spring action on it;
   wherein said first full-circle-ring stays open, with less than 360-degree full-circle coverage, when under pressure, pulling said first full-circle-ring apart, by said installer device;
   wherein said first full-circle-ring stays closed, with 360-degree full-circle coverage, in absence of any external pressure or force, by said installer device;
   said installer device comprising:
   a pair of handles;
   a pair of tips;
   a hinge;
   wherein said pair of tips are located at end of said pair of handles;
   wherein said hinge is located between said pair of handles;
   wherein said first full-circle-ring comprises two smaller rings or circles, located at an inner surface of said first full-circle-ring, and attached to said first full-circle-ring, configured for connection with said pair of tips of said installer device;
   wherein said first full-circle-ring is configured to be brought into a patient's heart, using said installer device, to attach to tissue of said patient's heart, by closing said first full-circle-ring and pinching said tissue;
   wherein said first set of one or more strings are configured to be connected to a first valve of said patient's heart.

2. The apparatus system for heart surgery, as recited in claim 1, said apparatus system comprises:
   a hook.

3. The apparatus system for heart surgery, as recited in claim 1, said apparatus system comprises:
   an arrow head.

4. The apparatus system for heart surgery, as recited in claim 1, wherein said first full-circle-ring is made of Titanium.

5. The apparatus system for heart surgery, as recited in claim 1, wherein said first full-circle-ring is made of metal.

6. The apparatus system for heart surgery, as recited in claim 1, wherein said first full-circle-ring is made of alloys.

7. The apparatus system for heart surgery, as recited in claim 1, wherein said-full-circle-ring is a hollow ring.

8. The apparatus system for heart surgery, as recited in claim 1, said apparatus system comprises a grabber part.

9. The apparatus system for heart surgery, as recited in claim 1, said apparatus system comprises a staple.

10. The apparatus system for heart surgery, as recited in claim 1, said apparatus system comprises a cup-shaped tip.

11. The apparatus system for heart surgery, as recited in claim 1, said apparatus system comprises a spring-loaded part.

12. The apparatus system for heart surgery, as recited in claim 1, said apparatus system comprises a light.

13. The apparatus system for heart surgery, as recited in claim 1, said apparatus system comprises a camera.

14. The apparatus system for heart surgery, as recited in claim 1, wherein said first set of one or more strings comprises 2 strings.

15. The apparatus system for heart surgery, as recited in claim 1, wherein said first set of one or more strings comprises 3 strings.

16. The apparatus system for heart surgery, as recited in claim 1, wherein said pair of handles are curved.

17. The apparatus system for heart surgery, as recited in claim 1, wherein said pair of handles are straight.

18. The apparatus system for heart surgery, as recited in claim 1, said apparatus system comprises non-toxic materials.

19. The apparatus system for heart surgery, as recited in claim 1, wherein said full-circle-ring is a stacked layer of circles.

* * * * *